(12) United States Patent
Sato et al.

(10) Patent No.: US 10,813,701 B2
(45) Date of Patent: Oct. 27, 2020

(54) SYSTEM, METHOD AND COMPUTER PROGRAM PRODUCT FOR BEND INFORMATION ESTIMATION

(71) Applicant: Olympus Corporation, Hachioji-shi, Tokyo (JP)

(72) Inventors: Ken Sato, Hachioji (JP); Hiromasa Fujita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 564 days.

(21) Appl. No.: 15/591,784

(22) Filed: May 10, 2017

(65) Prior Publication Data
US 2017/0239001 A1 Aug. 24, 2017

Related U.S. Application Data

(63) Continuation of application No. PCT/JP2014/080270, filed on Nov. 14, 2014.

(51) Int. Cl.
*A61B 1/00* (2006.01)
*A61B 34/20* (2016.01)
(Continued)

(52) U.S. Cl.
CPC ............ *A61B 34/20* (2016.02); *A61B 1/0002* (2013.01); *A61B 1/00004* (2013.01);
(Continued)

(58) Field of Classification Search
CPC ....... A61B 34/20; A61B 1/005; A61B 1/0002; A61B 1/00004; A61B 2034/2061;
(Continued)

(56) References Cited

U.S. PATENT DOCUMENTS

| 6,127,672 A | 10/2000 | Danisch |
| 2002/0183592 A1 | 12/2002 | Suzuki et al. |

(Continued)

FOREIGN PATENT DOCUMENTS

| JP | 2003-052613 A | 2/2003 |
| JP | 2003-150233 | 5/2003 |

(Continued)

OTHER PUBLICATIONS

Office Action for Corresponding Japanese Patent Application 2016-558845, 11pages.

(Continued)

*Primary Examiner* — Timothy J Neal
(74) *Attorney, Agent, or Firm* — Scully, Scott, Murphy & Presser, P.C.

(57) ABSTRACT

Example embodiments of the present invention relate to systems methods and computer program products for bend estimation. The system comprises a first and second light absorbers disposed at a substantially same position along an axis of a light guide and enabled to absorb first and second respective amounts of a plurality of wavelengths of a light transmitted along the light guide, a light detector enabled to detect respective intensities of the plurality of wavelengths of the light not absorbed by the first and second light absorbers, and a processor enabled to calculate a bend state of the light guide according to the detected intensities of the plurality of wavelengths of the light.

10 Claims, 21 Drawing Sheets

(51) Int. Cl.
*A61B 1/018* (2006.01)
*A61B 1/005* (2006.01)

(52) U.S. Cl.
CPC .......... *A61B 1/005* (2013.01); *A61B 1/00131* (2013.01); *A61B 1/018* (2013.01); *A61B 2034/2061* (2016.02)

(58) Field of Classification Search
CPC . A61B 1/018; A61B 1/00131; A61B 1/00167; A61B 1/0065
See application file for complete search history.

(56) References Cited

U.S. PATENT DOCUMENTS

| | | | | |
|---|---|---|---|---|
| 2007/0116415 | A1* | 5/2007 | Kobayashi | A61B 5/065 385/116 |
| 2014/0036261 | A1* | 2/2014 | Fujita | G01B 11/18 356/300 |
| 2014/0346331 | A1 | 11/2014 | Fujita | |
| 2015/0369592 | A1 | 12/2015 | Fujita et al. | |
| 2016/0166130 | A1 | 6/2016 | Fujita et al. | |
| 2017/0095143 | A1 | 4/2017 | Sato et al. | |
| 2017/0100196 | A1 | 4/2017 | Takayama et al. | |

FOREIGN PATENT DOCUMENTS

| | | | |
|---|---|---|---|
| JP | 2006-177684 | 7/2006 | |
| JP | 2007-143600 | 6/2007 | |
| JP | 2007-143600 A | 6/2007 | |
| JP | 2010-048058 | 3/2010 | |
| JP | 2011-245180 | 12/2011 | |
| JP | 2011-245180 A | 12/2011 | |
| JP | 2012-220241 | 11/2012 | |
| JP | 2013-164320 | 8/2013 | |
| JP | 2015-034787 | 2/2015 | |
| JP | 2016-007505 | 1/2016 | |
| JP | 2016-007506 | 1/2016 | |
| WO | WO-2012137846 A1 * | 10/2012 | ............. G01B 11/18 |

OTHER PUBLICATIONS

Office Action for Corresponding Japanese Patent Application 2016-558845, dated Nov. 13, 2018.
Pre-Appeal Examination Report from corresponding Japanese Patent Application 2016-558845, dated Apr. 9, 2019.
International Search Report and Written Opinion dated Feb. 24, 2015 issued in PCT/JP2014/080270, 5 pages.

* cited by examiner

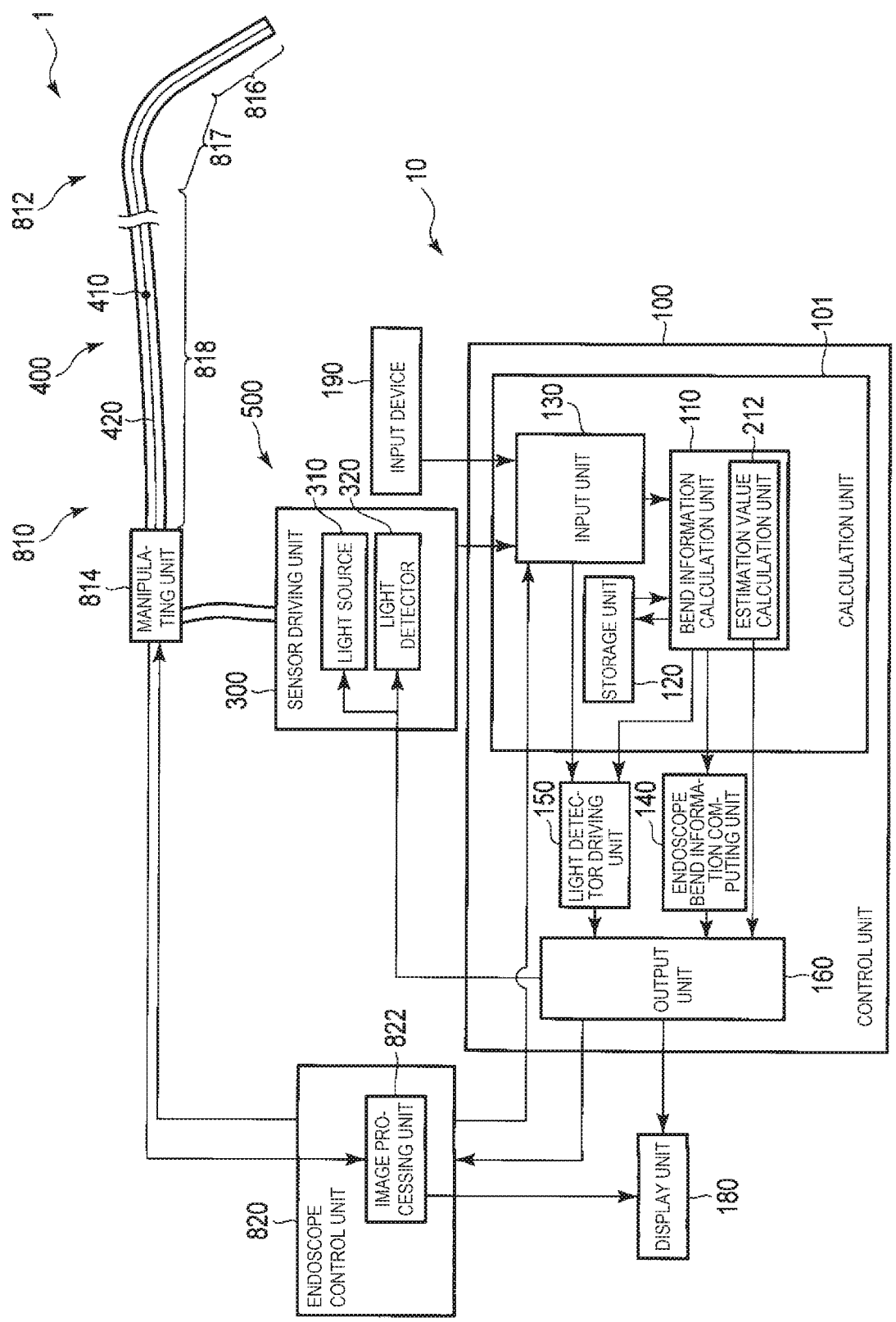
[FIG. 1]

[FIG. 2]
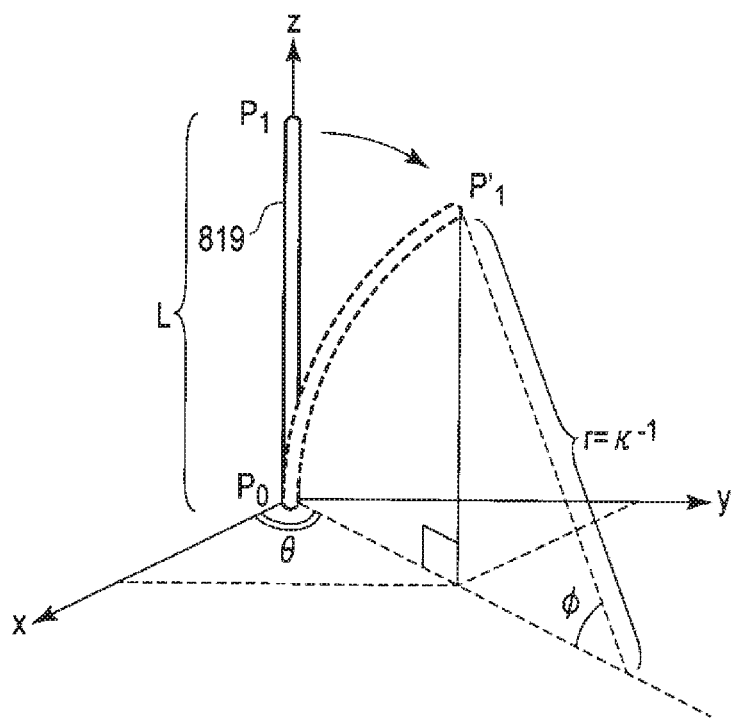

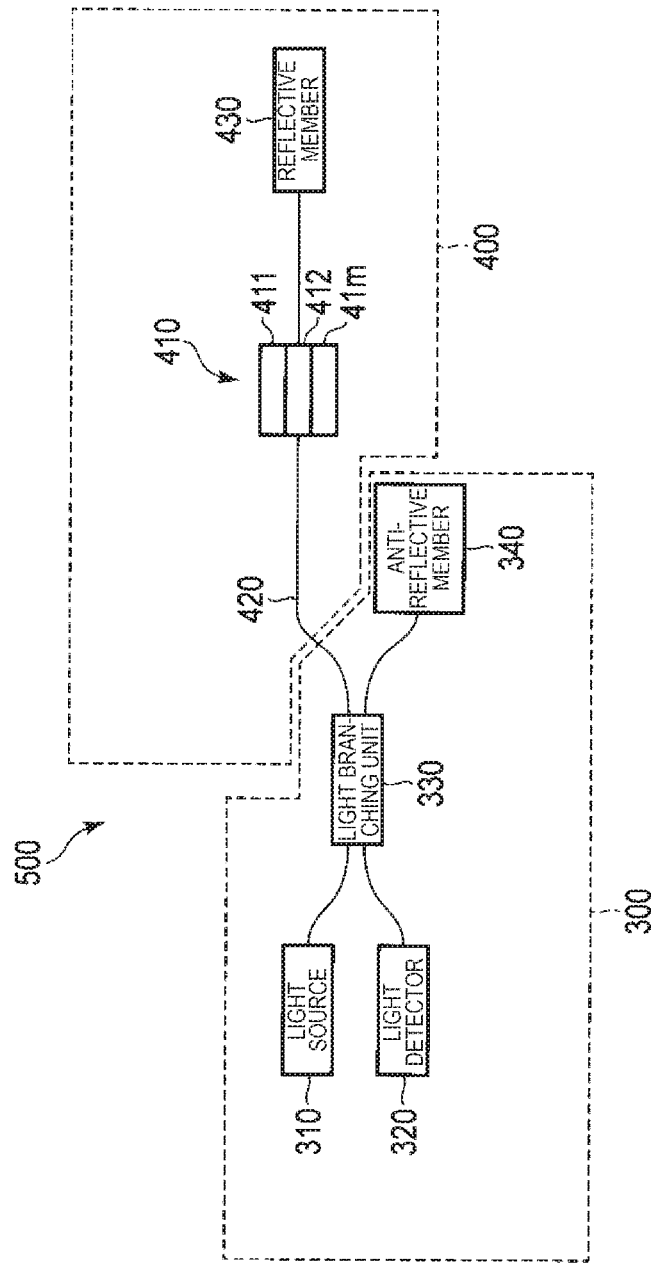
[FIG. 3]

[FIG. 4]
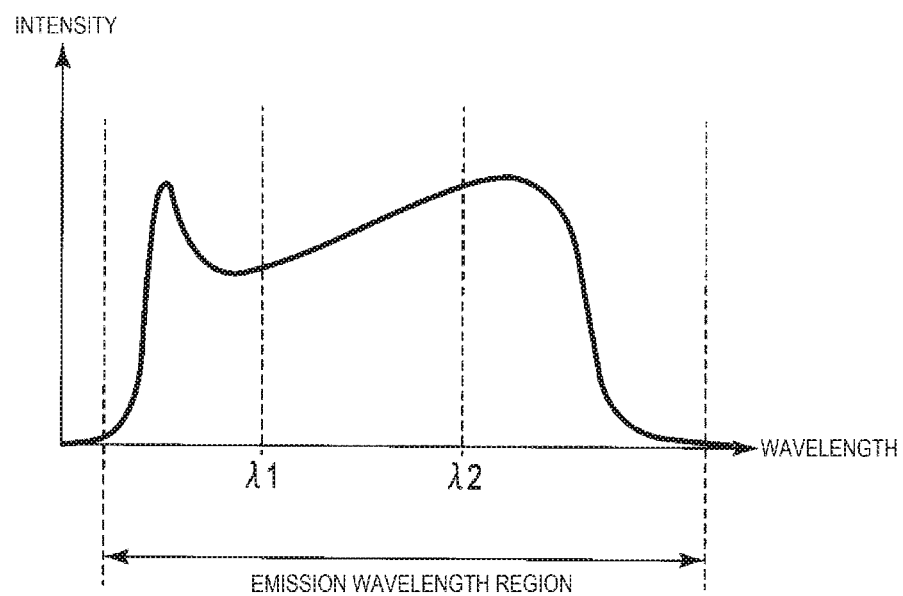
[FIG. 5]
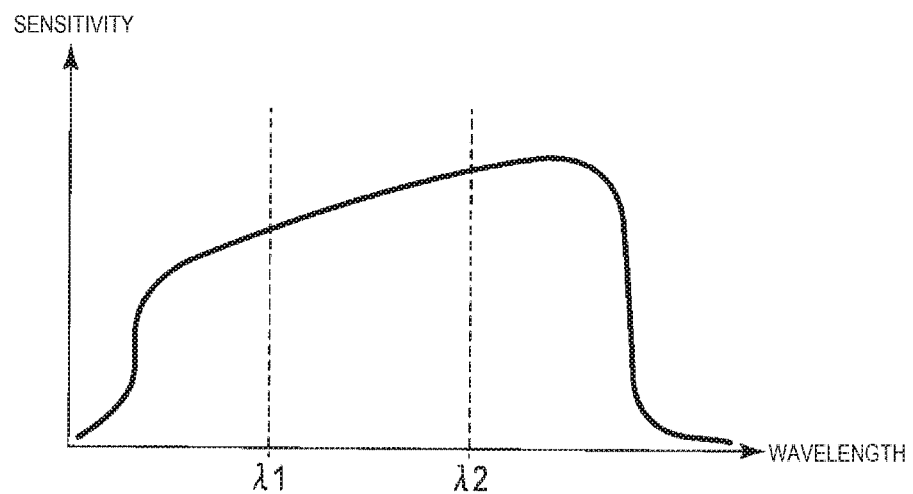

[FIG. 6]
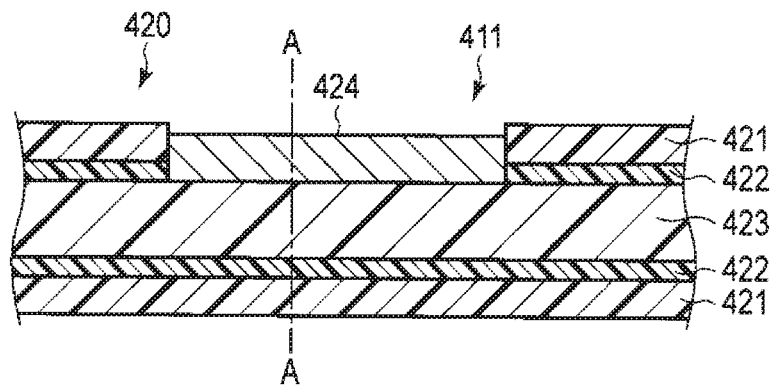
[FIG. 7]
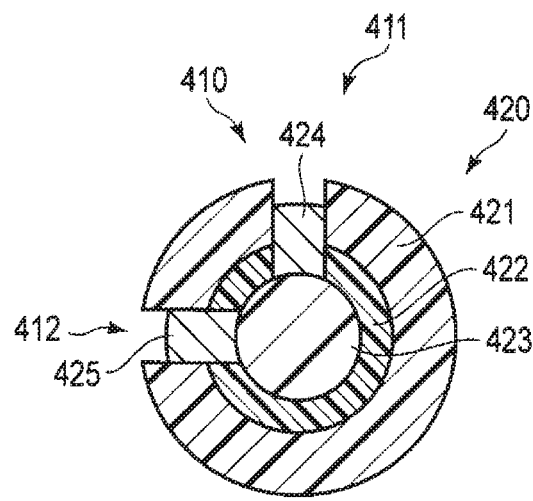

[FIG. 8]
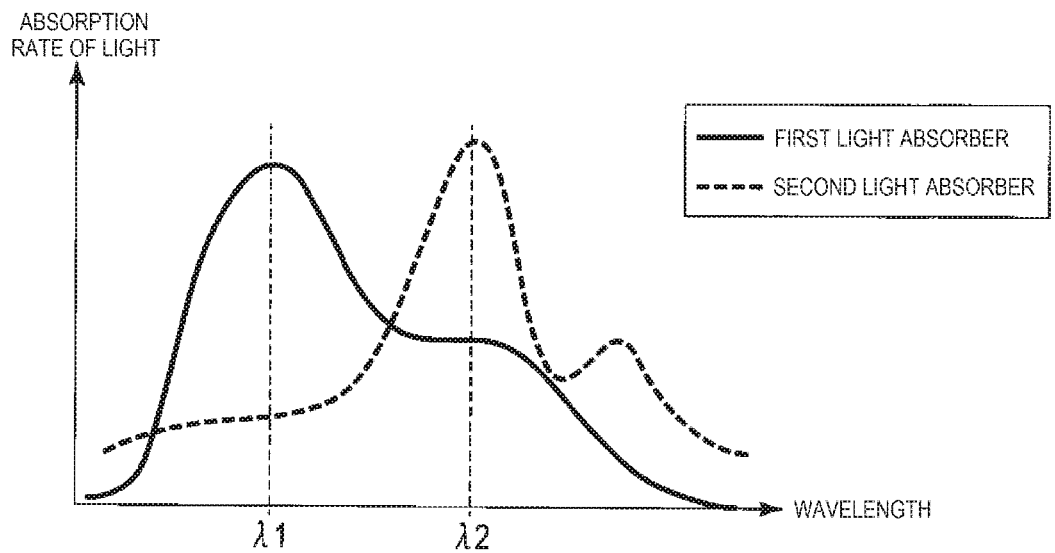
[FIG. 9A]
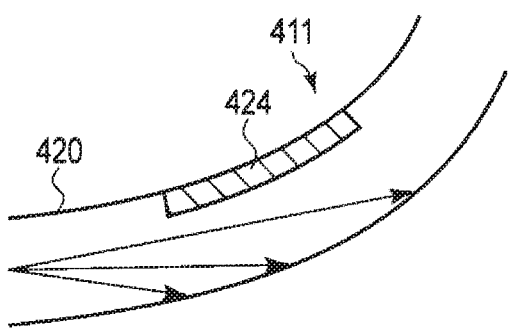
[FIG. 9B]
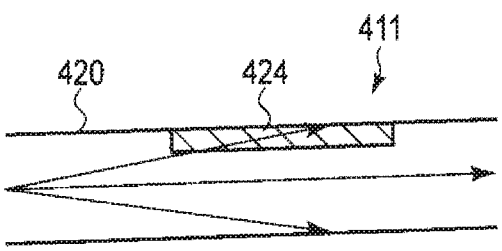

[FIG. 9C]
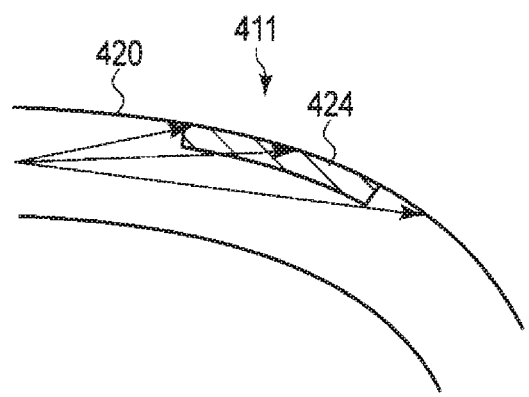
[FIG. 10]
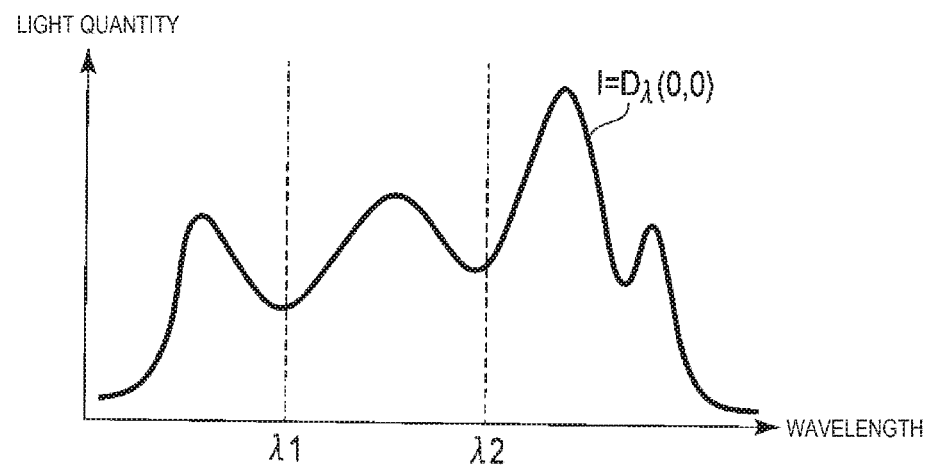

[FIG. 11]
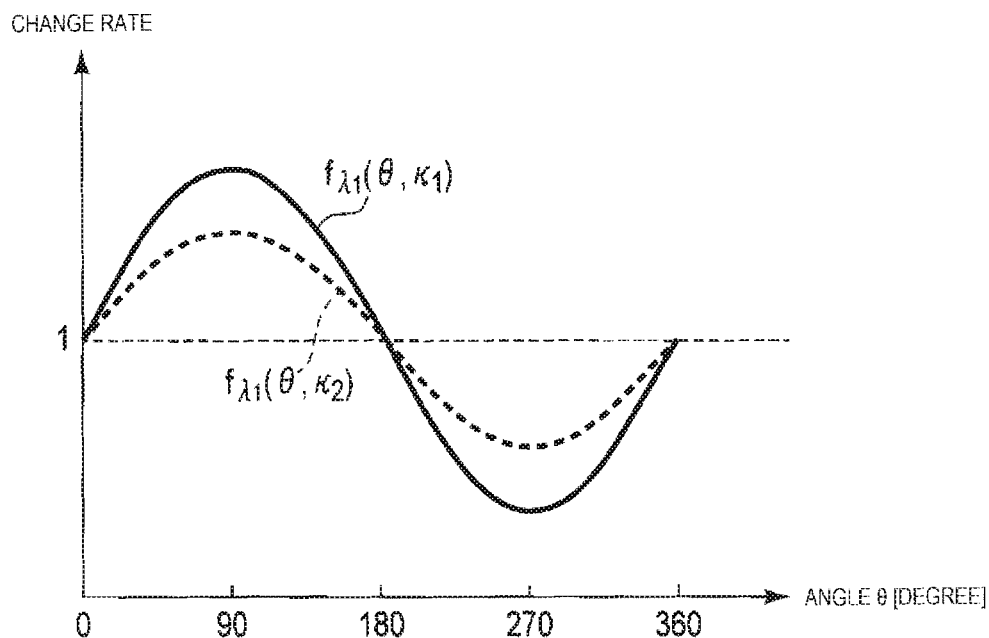
[FIG. 12]
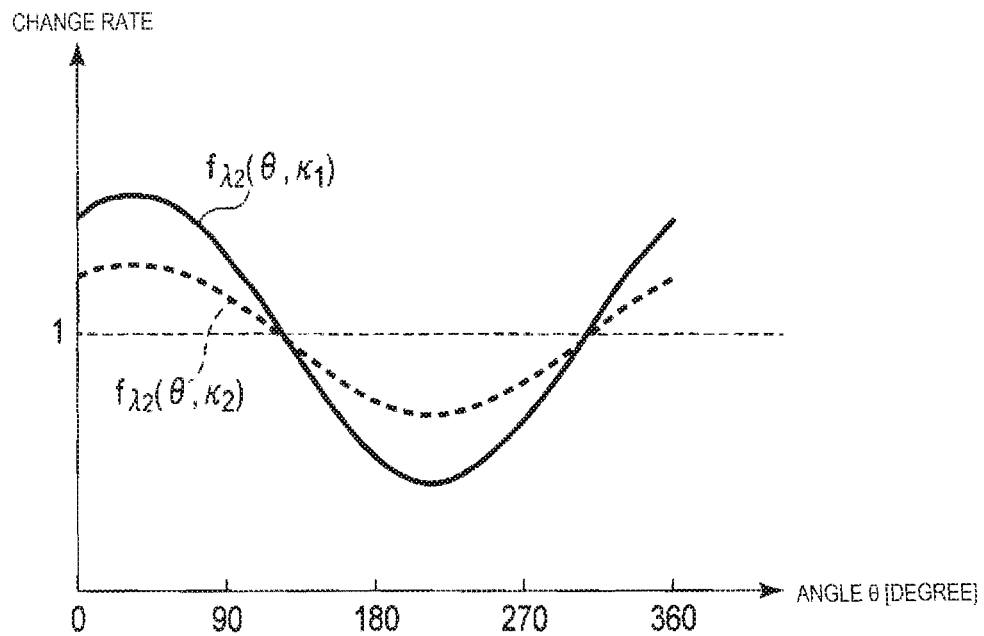

[FIG. 13]
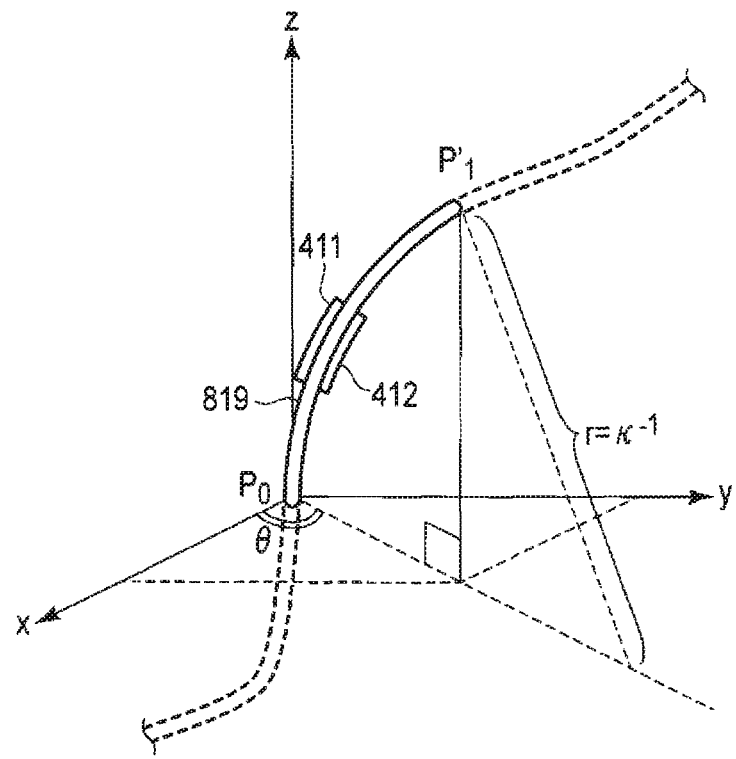
[FIG. 14]
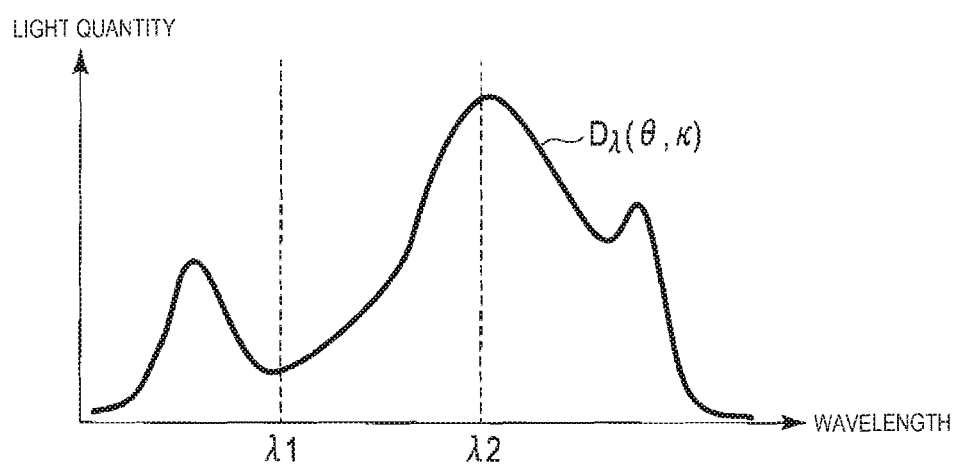

[FIG. 15]
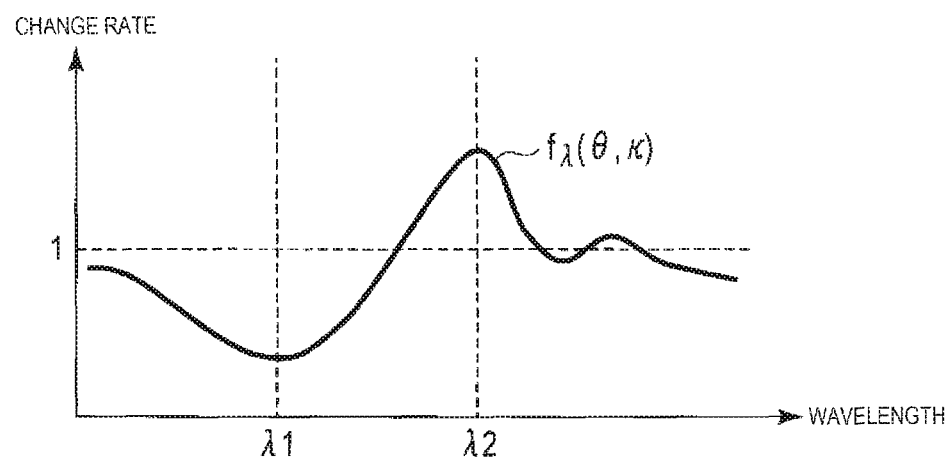

[FIG. 16]
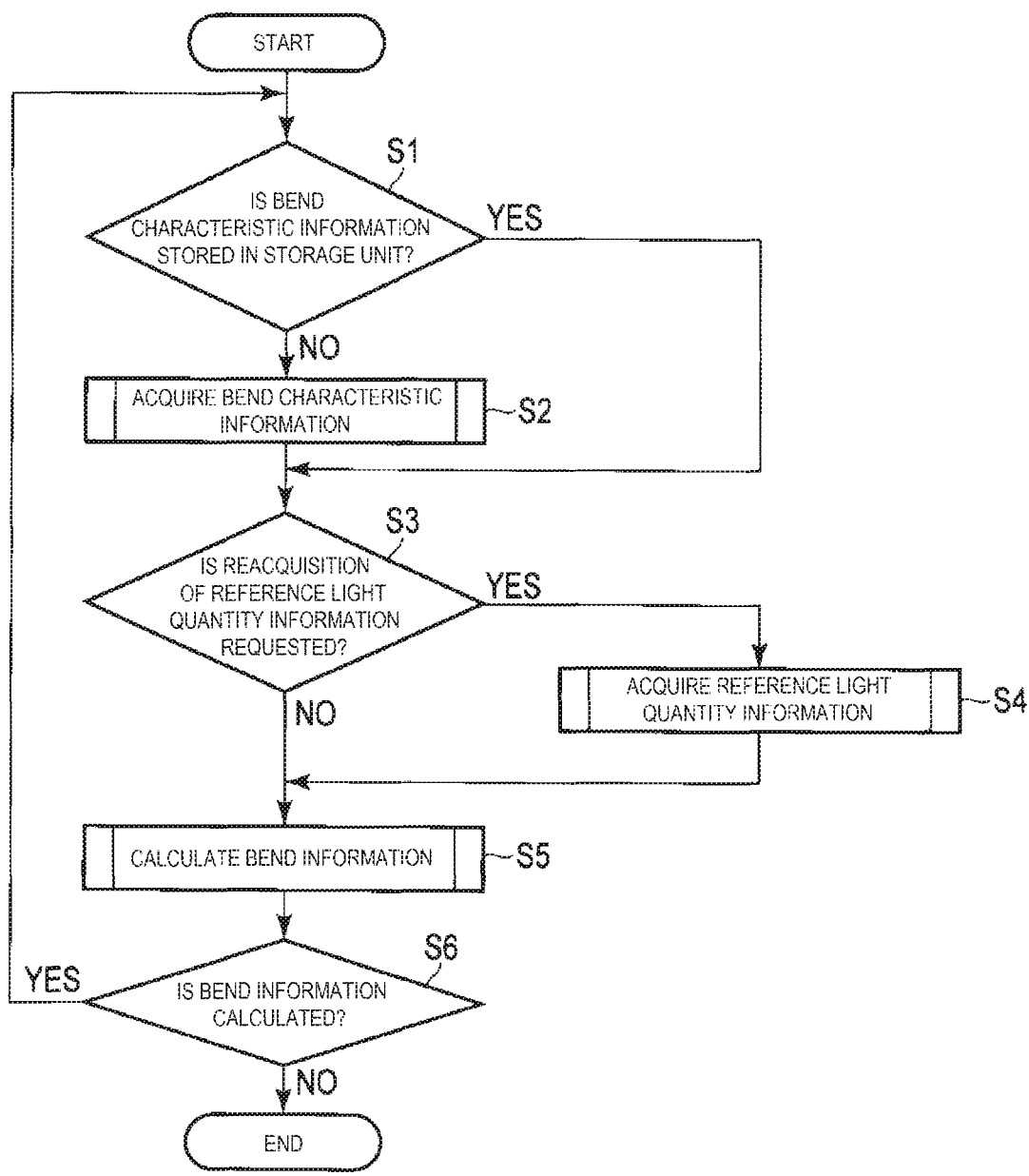

[FIG. 17]
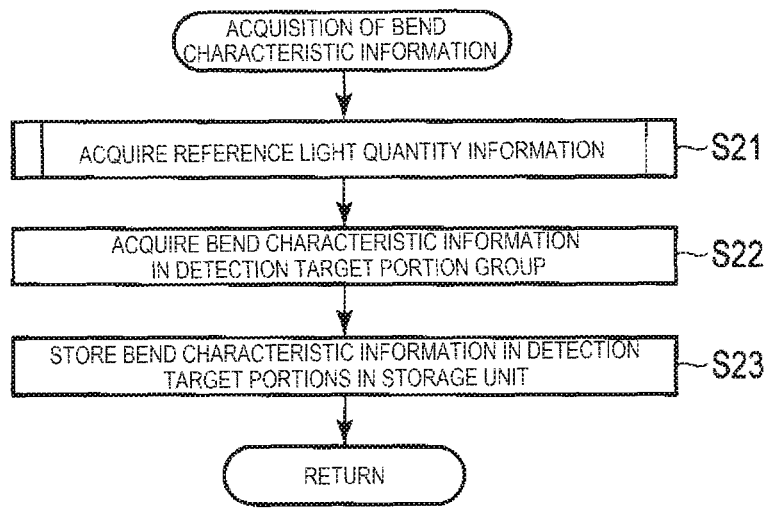
[FIG. 18]
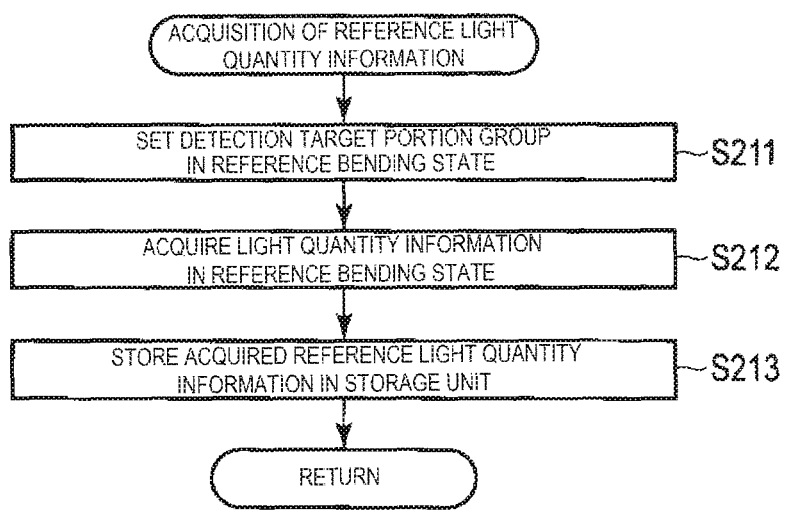

[FIG. 19]
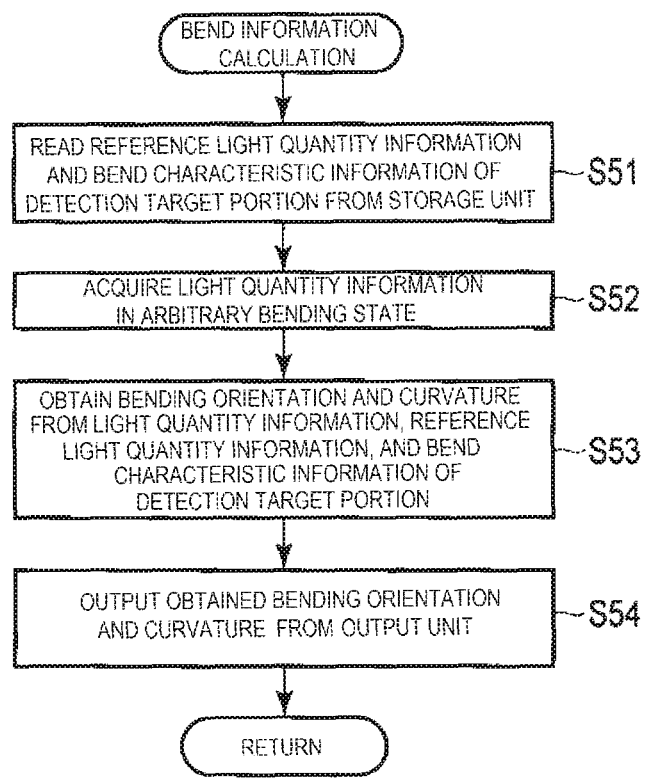

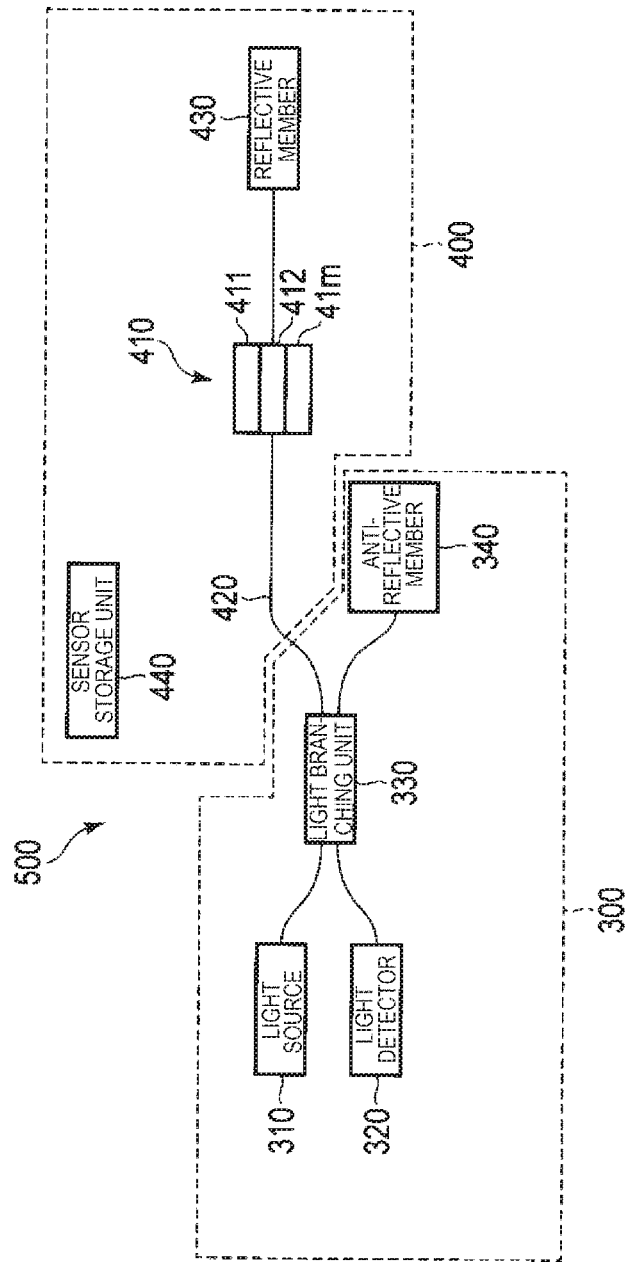
[FIG. 20]

[FIG. 21]
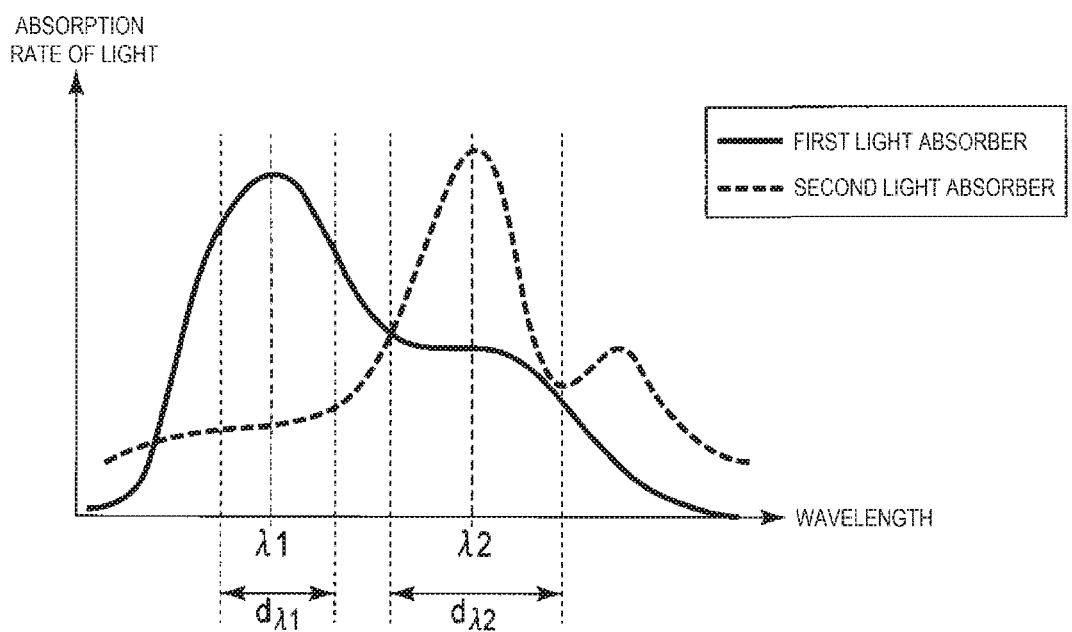
[FIG. 22]
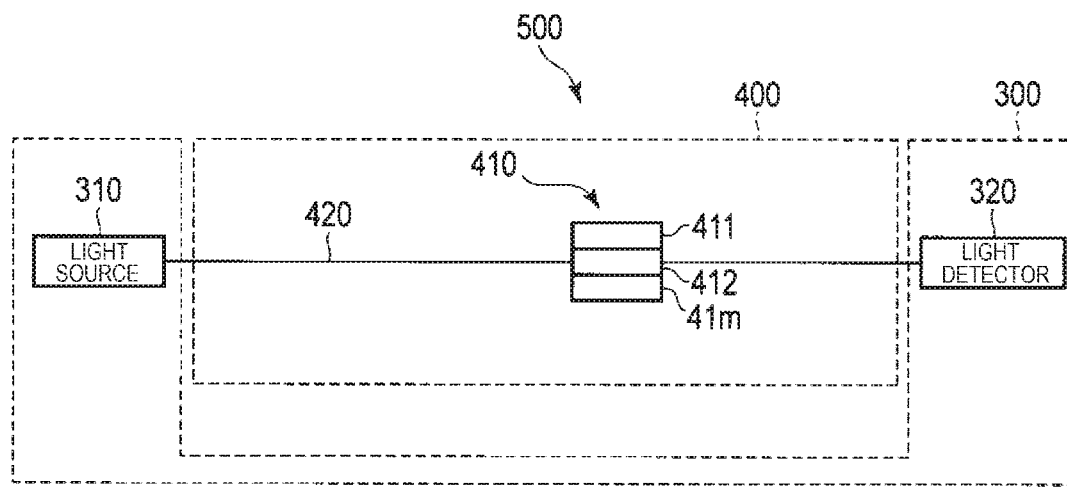

[FIG. 23]
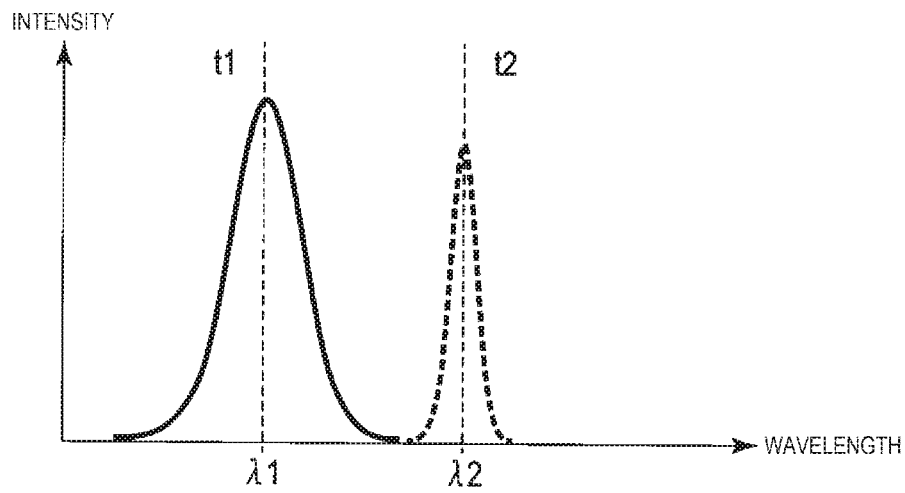
[FIG. 24]
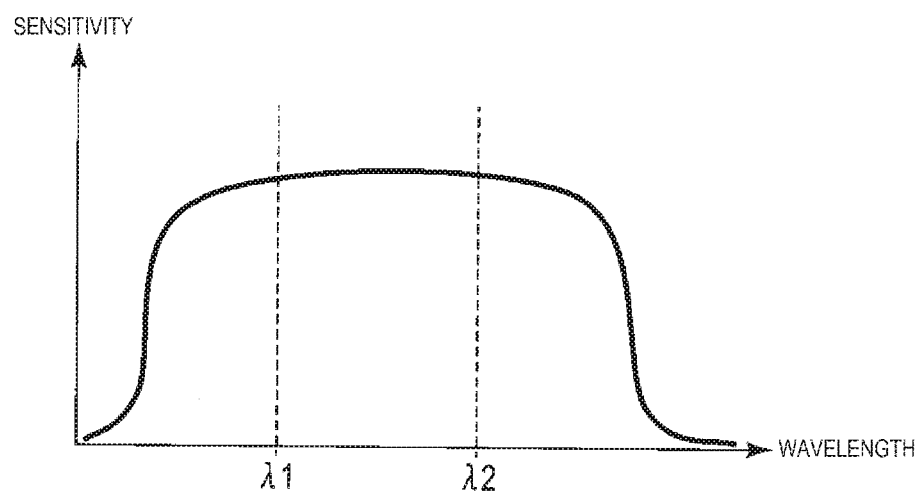

[FIG. 25]
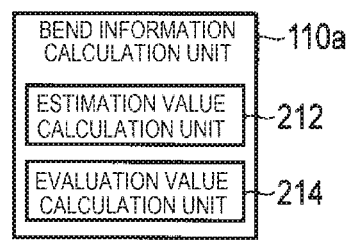
[FIG. 26]
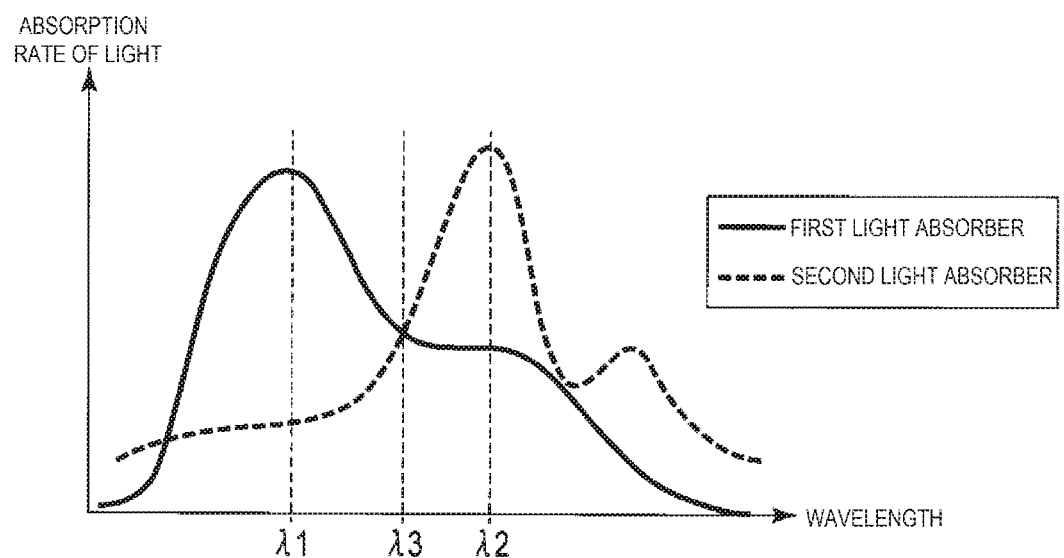

[FIG. 27]
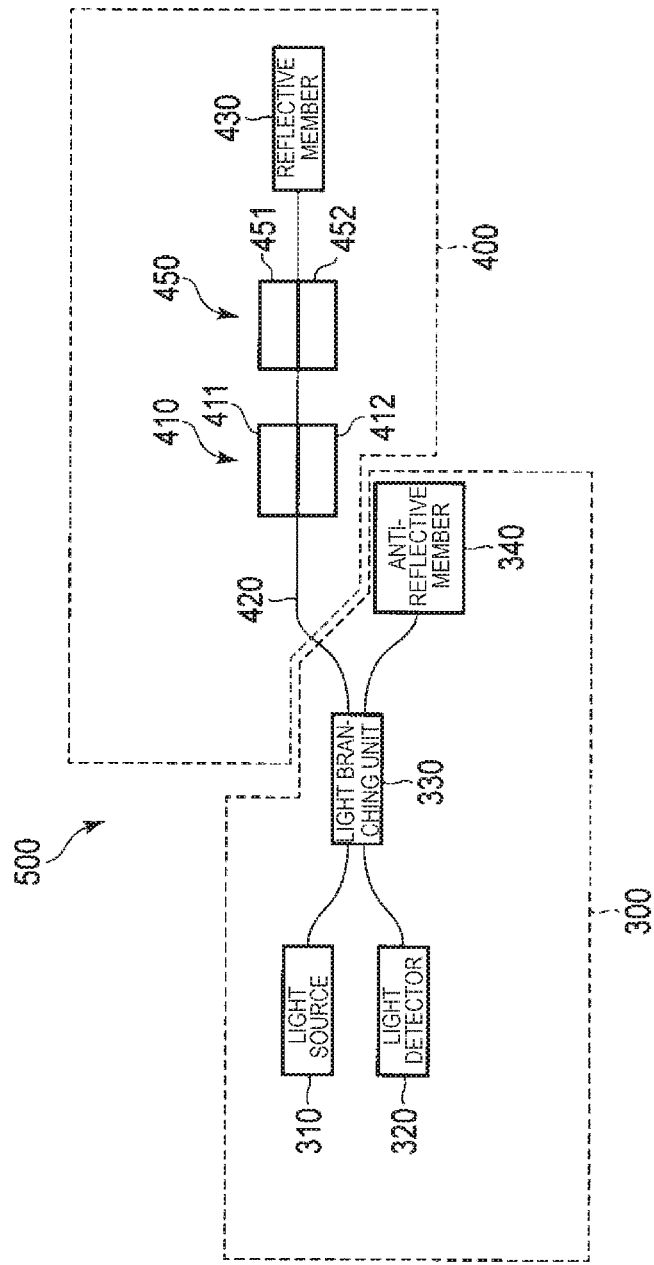

[FIG. 28]
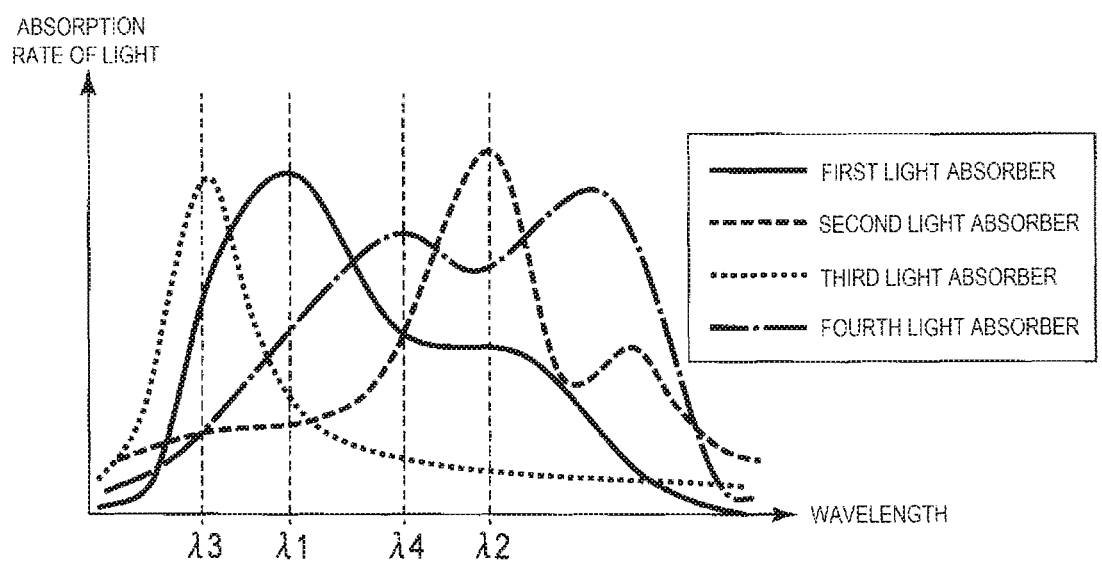

[FIG. 29A]
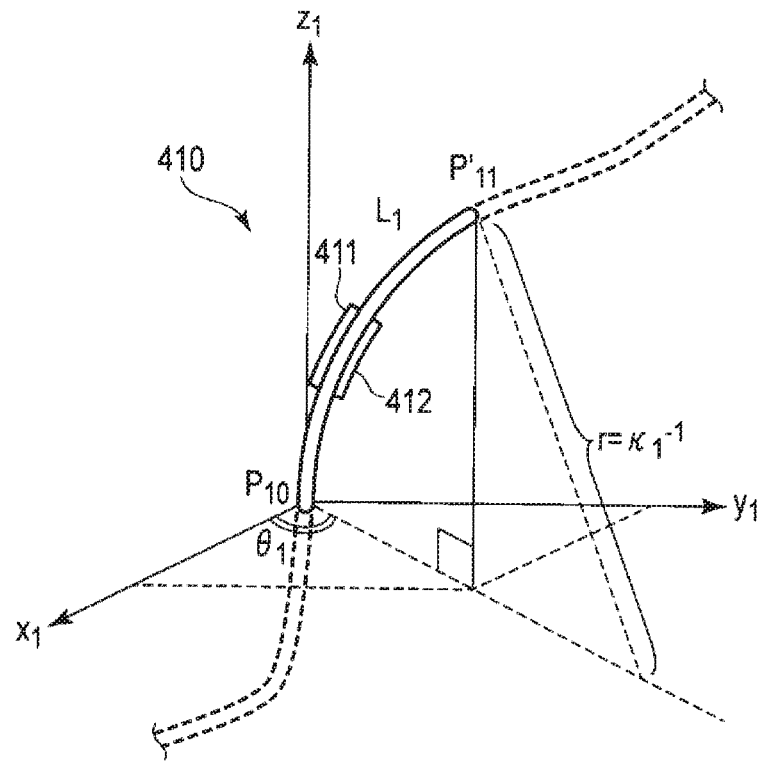
[FIG. 29B]
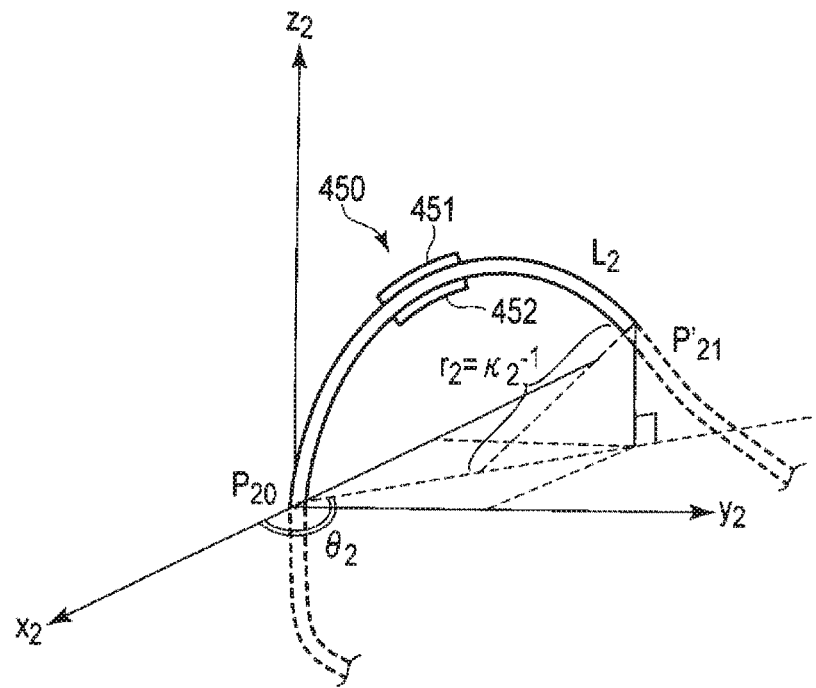

[FIG. 30]
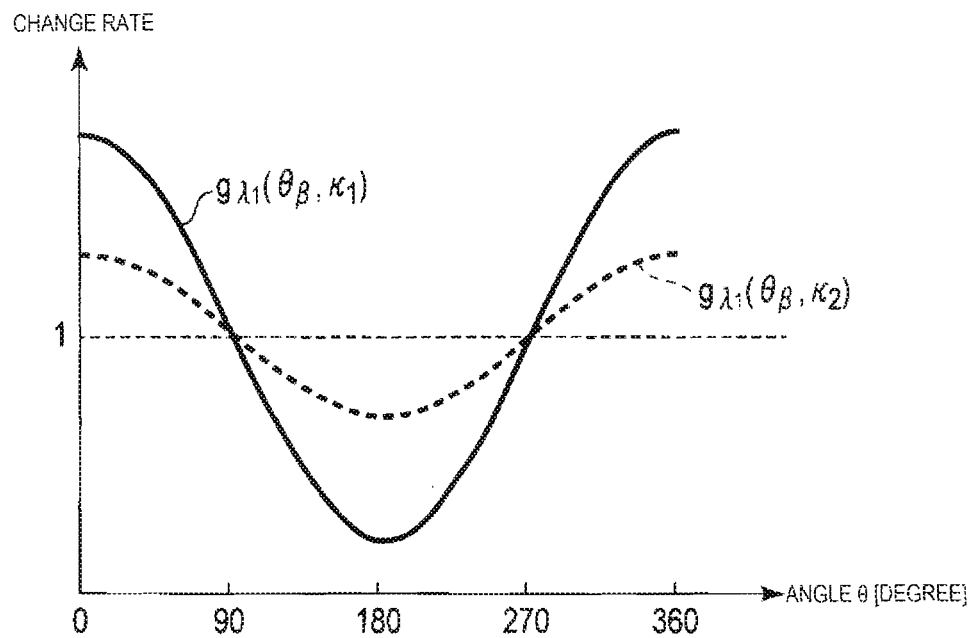
[FIG. 31]
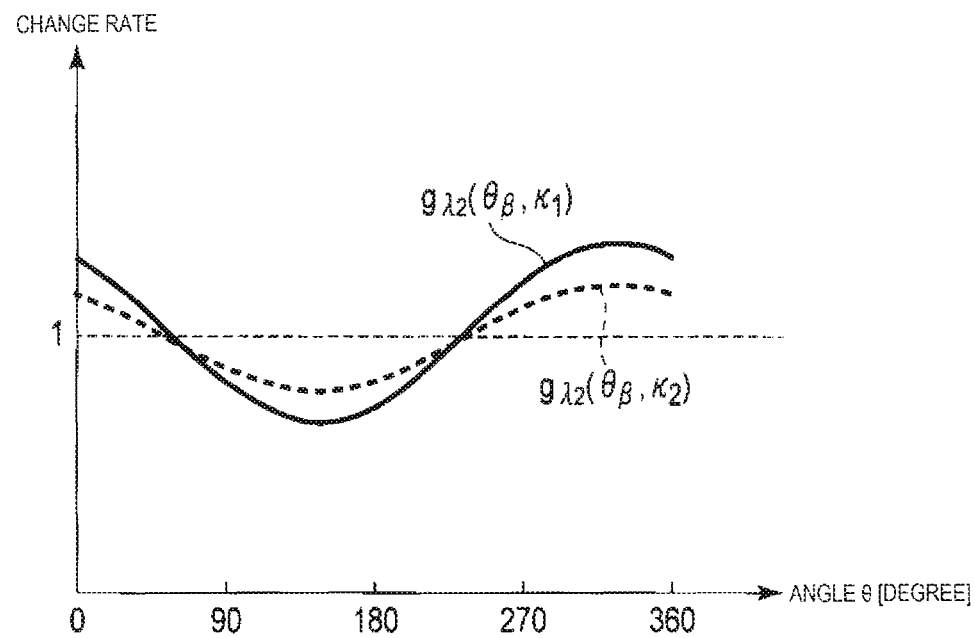

SYSTEM, METHOD AND COMPUTER PROGRAM PRODUCT FOR BEND INFORMATION ESTIMATION

CROSS-REFERENCE TO RELATED APPLICATION(S)

This application is a continuation application of PCT Application No. PCT/JP2014/080270 filed Nov. 14, 2014, which is hereby incorporated by reference in its entirety.

TECHNICAL FIELD

The present invention relates to a bend information estimation system, method and computer program product that estimates bend information representing a bending state of an object having flexibility.

BACKGROUND

In general, a device which is mounted in a flexible insertion portion of an insertion device (for example, an endoscope) and detects a bending state of the insertion portion has been known. For example, Japanese Patent Application Publication No. JP-A-2007-143600 discloses an endoscope shape detection probe using an optical fiber.

SUMMARY

Example embodiments of the present invention relate to systems and methods for bend estimation. The system comprises a first and second light absorbers disposed at a substantially same position along an axis of a light guide and enabled to absorb first and second respective amounts of a plurality of wavelengths of a light transmitted along the light guide, a light detector enabled to detect respective intensities of the plurality of wavelengths of the light not absorbed by the first and second light absorbers, and a processor enabled to calculate a bend state of the light guide according to the detected intensities of the plurality of wavelengths of the light.

BRIEF DESCRIPTION OF THE DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every Figure. The drawings are not necessarily to scale, emphasis instead being placed upon illustrating embodiments, principles, and concepts. Thus, features and advantages of the present disclosure will become more apparent from the following detailed description of exemplary embodiments thereof taken in conjunction with the accompanying drawings in which:

FIG. 1 is a diagram schematically illustrating a configuration of an endoscope system including a bend information estimation device of a first embodiment.

FIG. 2 is a diagram for describing an amount representing a bending state of a flexible portion.

FIG. 3 is a block diagram illustrating an example of a configuration of a sensor.

FIG. 4 is a diagram illustrating an example of a relationship between a wavelength and an intensity of light emitted from a light source.

FIG. 5 is a diagram illustrating an example of a relationship between a wavelength of light incident to a light detector and detection sensitivity of the light detector.

FIG. 6 is a sectional view including an optical axis of a light guiding member.

FIG. 7 is a sectional view of the light guiding member in a radial direction thereof, which is taken along line A-A in FIG. 6.

FIG. 8 is a diagram illustrating an example of a relationship between a wavelength and an absorption rate of light in a first light absorber and a second light absorber.

FIG. 9A is a diagram schematically illustrating transmission of light in a state in which a first detection target portion bends inward.

FIG. 9B is a diagram schematically illustrating transmission of light in a state in which the first detection target portion is in a straight line state.

FIG. 9C is a diagram schematically illustrating transmission of light in a state in which the first detection target portion bends outward.

FIG. 10 is a diagram illustrating an example of a relationship between a wavelength and a reference light quantity.

FIG. 11 is a diagram illustrating an example of bend characteristic information acquired with respect to a first wavelength.

FIG. 12 is a diagram illustrating an example of bend characteristic information acquired with respect to a second wavelength.

FIG. 13 is a diagram illustrating a state in which the flexible portion having a length of L, which includes a detection target portion group, bends at an angle θ and with curvature κ.

FIG. 14 is a diagram illustrating an example of a detected light quantity in a bending state in FIG. 13.

FIG. 15 is a diagram illustrating an example of a relationship between a wavelength and a change rate of a light quantity in the detection target portion group.

FIG. 16 is a flowchart illustrating flow of a process in a control unit.

FIG. 17 is a flowchart illustrating an example of acquisition of the bend characteristic information.

FIG. 18 is a flowchart illustrating an example of acquisition of reference light quantity information.

FIG. 19 is a flowchart illustrating an example of a bend information calculation process.

FIG. 20 is a block diagram illustrating another example of a configuration of a sensor.

FIG. 21 is a diagram illustrating another example of a relationship between a wavelength and an absorption rate of light in a first light absorber and a second light absorber.

FIG. 22 is a block diagram illustrating another example of a configuration of a sensor.

FIG. 23 is a diagram illustrating an example of a relationship between a wavelength and an emission intensity of the light source at a certain time point.

FIG. 24 corresponds to FIG. 23 and is a diagram illustrating a relationship between the wavelength of light incident to the light detector and detection sensitivity of the light detector.

FIG. 25 is a block diagram illustrating an example of a bend information calculation unit according to a second embodiment.

FIG. 26 is a diagram illustrating another example of a relationship between a wavelength and an absorption rate of light in a first light absorber and a second light absorber.

FIG. 27 is a block diagram illustrating an example of a configuration of a sensor according to a third embodiment.

FIG. 28 is a diagram illustrating another example of a relationship between a wavelength and an absorption rate of light in first, second, third, and fourth light absorbers.

FIG. 29A is a diagram illustrating a state in which a region having a length of $L_1$, of a flexible portion, which includes a first detection target portion group, bends at an angle $\theta_1$ and with curvature $\kappa_1$.

FIG. 29B is a diagram illustrating a state in which a region having a length of $L_2$, of a flexible portion, which includes a second detection target portion group, bends at an angle $\theta_2$ and with curvature $\kappa_2$.

FIG. 30 is a diagram illustrating an example of bend characteristic information acquired with respect to a first wavelength associated with the second detection target portion group.

FIG. 31 is a diagram illustrating an example of bend characteristic information acquired with respect to a second wavelength associated with the second detection target portion group.

DETAILED DESCRIPTION

As described in Japanese Patent Application Publication No. JP-A-2007-143600, the detection probe includes the optical fiber that integrally bends with an insertion portion of an endoscope. The optical fiber is provided with two light modulating units substantially at the same positions in a longitudinal direction of the optical fiber. The light modulating unit detects curvature in two directions of, for example, an X direction and a Y direction. The light modulating unit modulates an intensity or the like of a wavelength component of light transmitting through the optical fiber. In the probe, the light modulating unit detects the curvature of the optical fiber and further curvature of the insertion portion that integrally bends with the optical fiber, based on the intensity or the like of the wavelength component obtained before and after light passes through the light modulating unit.

However, the prior art does not disclose a specific method for calculating the curvatures in the two directions (magnitude of the bending) based on the intensity or the like of the wavelength component. In addition, a specific method for calculating a bending orientation of the optical fiber along with the curvature is not disclosed.

Therefore, example embodiments of the present invention provide a bend information estimation device that is capable of estimating bend information (a bending orientation and a magnitude of bending), an endoscope system including the bend information estimation device, a bend information estimating method, and a program for estimating bend information.

According to the present invention, it is possible to provide a bend information estimation device that is capable of estimating bend information, an endoscope system including the bend information estimation device, a bend information estimating method, and a program for estimating bend information.

FIG. 1 is a diagram schematically illustrating a configuration of an endoscope system 1 including a bend information estimation device 10 (hereinafter, referred to as an estimation device 10) according to an example embodiment of the present invention. The endoscope system 1 includes an endoscope 810, an endoscope control unit 820, the estimation device 10, a display unit 180, and an input device 190.

The endoscope 810 includes an elongate insertion portion 812 that is inserted into an insertion target body, and a manipulating unit 814 connected to a base end side of the insertion portion 812. The insertion portion 812 includes a hard front end portion 816, a bending portion 817 provided on the base end side of the hard front end portion 816, and a flexible tube portion 818 provided on the base end side of the bending portion 817. The hard front end portion 816 is provided with an illumination optical system, an observation optical system, an imaging device, or the like, which are not illustrated in figures. The bending portion 817 bends in a desired direction in response to manipulation of the manipulating unit 814. The flexible tube portion 818 freely bends. The manipulating unit 814 is used to perform various types of manipulation of the endoscope 810 including the bending manipulation described above.

The endoscope control unit 820 controls various operations of the endoscope 810. In addition, the endoscope control unit 820 includes an image processing unit 822 for performing processes on an image acquired by the observation optical system and the imaging device described above.

The estimation device 10 is a device for estimating bend information representing a bending state of the insertion portion 812, particularly, the bending portion 817 and the flexible tube portion 818 (hereinafter, referred to as a flexible portion 819, as illustrated in FIG. 2). The estimation device 10 includes a sensor 500 configured to have a sensor driving unit 300 and a sensor unit 400, and a control unit 100 (described in greater detail below with reference to FIG. 3).

The display unit 180 may be a common display device (e.g., a liquid crystal display, a CRT display, and an organic EL display). The display unit 180 is connected to the endoscope control unit 820 and displays an image processed in the endoscope control unit 820. In addition, the display unit 180 is connected to the control unit 100 and displays the bend information or the like obtained by the estimation device 10.

The input device 190 may be a common input device (e.g., a keyboard, a pointing device such as a mouse, a tag reader, a button switch, a slider, and a dial). The input device 190 is connected to the control unit 100. The input device 190 is used to input various instructions such that a user operates the estimation device 10. The input device 190 may be a storage medium. In this case, information stored in the storage medium is input to the control unit 100.

FIG. 2 is a diagram illustrating a bending state of a flexible portion according to an example embodiment of the present invention. As illustrated in FIG. 2, the flexible portion 819 has a length L, which is positioned to have a straight line shape from an origin $P_0$ (0, 0, 0) to a point $P_1$ (0, 0, L), is illustrated in a solid line according to an example embodiment of the present invention. The flexible portion 819 bends as illustrated in a dashed line in FIG. 2, and the point $P_1$ (0, 0, L) is shifted to a point $P'_1$ (x, y, z). Here, the flexible portion 819 is described to bend to have an arc shape, for convenience. According to the example embodiment illustrated in FIG. 2, in order to describe a bending state of the flexible portion 819, two items of information of a bending orientation (or bend orientation) and a magnitude of the bending (or bend magnitude) need to be obtained. The bend orientation and bend magnitude can comprise a bend state. The bending orientation is represented by, for example, an angle $\theta$ formed between an x axis and a straight line through the origin $P_0$ (0, 0, 0) and a point (x, y, 0) obtained by projecting the point $P'_1$ (x, y, z) to an xy plane. In addition, the magnitude of the bending is represented by, for example, curvature κ, curvature radius $r=κ^{-1}$, a central angle $φ=L/r=κL$, or the like. As described above, according to example embodiments of the present invention, the bending orientation and the magnitude of the bending required to describe the bending state of the flexible portion 819 are referred to as the bend information.

FIG. 3 is a block diagram illustrating an example of a configuration of the sensor 500 of the estimation device 10 configured to have a sensor driving unit 300 and a sensor unit 400 according to an example embodiment of the present invention. The sensor driving unit 300 includes a light source 310, a light detector 320, a light branching unit 330, and an antireflective member 340. The sensor unit 400 includes a light guiding member (also referred to herein as a light guide) 420 provided with a detection target portion group (also referred to herein as a detection target group) 410 including a plurality of detection target portions, and a reflective member 430.

The light source 310 may be a commonly known light emitting portion such as a lamp, an LED, or a laser diode. The light source 310 further may have a fluorescent substance for converting a wavelength, and the like.

FIG. 4 is a diagram illustrating an example of a relationship between a wavelength and an intensity of light emitted from the light source 310. The light source 310 emits light having an emission wavelength range including a first wavelength λ1 and a second wavelength λ2. The first wavelength λ1 is a characteristic wavelength of a spectrum that is absorbed by a light absorber (hereinafter, referred to as a first light absorber 424) of a first detection target portion 411 that configures the detection target portion group 410. Here, the characteristic wavelength means a wavelength with which the highest absorption is performed, for example, (refer to FIG. 8). Similarly, the second wavelength λ2 is a characteristic wavelength of a spectrum that is absorbed by a light absorber (hereinafter, referred to as a second light absorber 425) of a second detection target portion 412 that configures the detection target portion group 410.

The light detector 320 includes an element such as a spectroscope or a color filter for dispersing light, and a light receiving element such as a photodiode. The light detector 320 detects an intensity of light of a predetermined wavelength range and outputs light quantity information. Here, the light quantity information is information representing a relationship between a specific wavelength in the predetermined wavelength range and a light intensity with the wavelength.

FIG. 5 is a diagram illustrating an example of a relationship between a wavelength of light incident to the light detector 320 and detection sensitivity of the light detector 320. The light detector 320 has detection sensitivity within a wavelength range including the first wavelength λ1 and the second wavelength λ2 described above. The light detector 320 outputs, to the control unit 100, the light quantity information representing light intensity detected with the wavelengths λ1 and λ2, for example.

Note that the light detector is not limited to a light detector having spectral characteristics. The light source and the light detector include an example of a configuration in which a light source and a light detector are combined, thereby detecting a light quantity for each of a plurality of predetermined wavelength range. For example, the light source and the light detector include an example of configuration in which narrow-band light is emitted from the light source at time intervals in order, and light quantities in wavelength ranges are detected by a broad band light detector.

With reference to FIG. 3, the light branching unit 330 is optically connected to the light source 310 and the light detector 320. The light branching unit 330 includes an optical coupler, a half mirror, or the like. The light branching unit 330 guides the light emitted from the light source 310 to the light guiding member 420 and guides, to the light detector 320, the light guided by the light guiding member 420.

The antireflective member 340 is optically connected to the light branching unit 330. The antireflective member 340 prevents light, which is not incident to the light guiding member 420 of the light emitted from the light source 310, from returning to the light detector 320.

The light guiding member 420 is, for example, an optical fiber and is flexible. A base end of the light guiding member 420 is connected to the light branching unit 330. The light guiding member 420 is incorporated in the insertion portion 812 in a longitudinal direction thereof, as schematically illustrated in FIG. 1. The light guiding member 420 is provided with the detection target portion group 410 disposed on the flexible portion 819 at a position of the insertion portion 812, which is considered to be necessary to have the calculated bend information.

As illustrated in FIG. 3, the detection target portion group 410 includes at least the first detection target portion 411 and the second detection target portion 412, and may further include an m-th detection target portion 41m. Here, m is an arbitrary number. The detection target portions 411, 412, . . . , and 41m are provided substantially at the same position of the light guiding member 420 in the longitudinal direction (optical axis direction) thereof. Hereinafter, the detection target portion group 410 is described to be configured to have the first detection target portion 411 and the second detection target portion 412.

FIG. 6 is a sectional view including an optical axis of the light guiding member 420 according to an example embodiment of the present invention. FIG. 7 is a sectional view of the light guiding member 420 in a radial direction thereof, which is taken along line A-A in FIG. 6, according to an example embodiment of the present invention. FIGS. 6 and 7 will be described in conjunction.

The light guiding member 420 includes a core 423, a clad 422 that surrounds the core 423, and a jacket 421 that surrounds the clad 422. A part of the jacket 421 and the clad 422 is removed and the core 423 is exposed such that the first detection target portion 411 is formed with the first light absorber 424 provided on the exposed core 423. The second detection target portion 412 is provided substantially at the same position as the first detection target portion 411 in the longitudinal direction of the light guiding member 420 and at a position, for example, substantially orthogonal to the first detection target portion 411 in a cross section of the light guiding member 420 in a radial direction thereof. The second detection target portion 412 is formed with the second light absorber 425 provided in the same manner as the first detection target portion 411. Note that, without limiting to the light absorber, it is possible to use an optical member having an effect on a spectrum of the guided light, and the optical member may be, for example, a wavelength converting member (e.g., fluorescent substance).

FIG. 8 is a diagram illustrating an example of a relationship between a wavelength and an absorption rate of light in the first light absorber 424 and the second light absorber 425. As illustrated in FIG. 8, the light absorbers 424 and 425 provided in different detection target portions 411 and 412 have a light absorption rate different for each wavelength (i.e., light absorption characteristics different from each other).

FIGS. 9A to 9C are diagrams schematically illustrating light guided to the vicinity of the first detection target portion 411 of the light guiding member 420. It should be understood that a relationship exists between the bending states of the detection target portions 411 and 412 and a transmission amount of light guided through the light guiding member 420. In FIGS. 9A to 9C, the second detection target portion 412 is not illustrated. As illustrated in FIG. 9B, in a case where the light guiding member 420 is in a straight line state, a part of light guided through the light guiding member 420 is absorbed into the light absorber 424. In this respect, in a case where the light guiding member 420 bends such that the light absorber 424 is positioned inward as illustrated in FIG. 9A, light reaching the light absorber 424 is reduced and, thus, an amount of light absorption by the light absorber 424 decreases. Hence, the transmission amount of light guided through the light guiding member 420 increases. On the other hand, in a case where the light guiding member 420 bends such that the detection target portion group 410 is positioned outward as illustrated in FIG. 9C, light reaching the light absorber 424 increases, and thus an amount of light absorption by the light absorber 424 increases. Hence, the transmission amount of light guided through the light guiding member 420 decreases.

As described above, an amount of light guided through the light guiding member 420 is changed depending on the bending state of the first detection target portion 411. The same is true of the second detection target portion 412. In the following description, the bending of the light guiding member 420 in a direction in which the transmission amount of light increases is referred to as the bending in a positive direction as illustrated in FIG. 9A and the bending of the light guiding member 420 in a direction in which the transmission amount of light decreases is referred to as the bending in a negative direction as illustrated in FIG. 9C.

With reference to FIG. 3 again, the reflective member 430 is provided in an end portion of the light guiding member 420 on a side on which the end portion is not connected to the light branching unit 330 (i.e., a front end). The reflective member 430 reflects the light guided by the light guiding member 420 from the light branching unit 330 such that the light returns in a direction toward the light branching unit 330.

Next, the control unit 100 of the estimation device 10 will be described with reference to FIG. 1 again. The control unit 100 can be configured of an electronic computer such as a personal computer. The control unit 100 includes a calculation unit 101, an endoscope bend information computing unit 140, a light detector driving unit 150, and an output unit 160. The calculation unit 101 is configured of a device or the like including a CPU, an ASIC, or the like. The calculation unit 101 includes an input unit 130, a storage unit 120, and a bend information calculation unit 110.

The light quantity information is input to the input unit 130 from the light detector 320 of the sensor driving unit 300. The input unit 130 transmits the input light quantity information to the bend information calculation unit 110. In addition, bend characteristic information of the detection target portion group 410, which will be described below, is input to the input unit 130. Further, information output from the endoscope control unit 820 is also input to the input unit 130. The input unit 130 transmits the input information to the bend information calculation unit 110 or the light detector driving unit 150.

The storage unit 120 stores various items of information required in calculation performed in the bend information calculation unit 110. The storage unit 120 can be a memory. The storage unit 120 stores a program including calculation algorithms and a light quantity estimation relationship including the bend characteristic information of the detection target portion group 410, which will be described below, or the like.

The bend information calculation unit 110 calculates the bend information of the detection target portion group 410 based on the light quantity information acquired via the input unit 130 and the light quantity estimation relationship stored in the storage unit 120, which will be described below. The bend information calculation unit 110 includes an estimation value calculation unit 212. The estimation value calculation unit 212 generates a light quantity estimation value, based on the light quantity estimation relationship stored in the storage unit 120. The bend information calculation unit 110 calculates the bend information of the detection target portion group 410, based on the light quantity information acquired via the input unit 130 and the generated light quantity estimation value. The bend information calculation unit 110 transmits the calculated bend information to the endoscope bend information computing unit 140 and the output unit 160. In addition, the bend information calculation unit 110 outputs, to the light detector driving unit 150, information related to an operation of the light detector 320, such as a gain of the light detector 320, which is required to calculate the bend information.

The endoscope bend information computing unit 140 includes, for example, a CPU, an ASIC, or the like. The endoscope bend information computing unit 140 calculates bend information of the insertion portion 812 on which the detection target portion group 410 is disposed, based on the bend information of the detection target portion group 410, which is calculated in the bend information calculation unit 110. The calculated bend information is transmitted to the output unit 160. Note that the endoscope bend information computing unit 140 may be incorporated in the bend information calculation unit 110.

The light detector driving unit 150 generates a drive signal of the light detector 320, based on the information acquired from the input unit 130 or the bend information calculation unit 110. In response to the drive signal, for example, the light detector driving unit 150 switches between on and off of the operation of the light detector 320, based on an instruction from a user, which is acquired via the input unit 130, or adjusts the gain of the light detector 320, based on the information acquired from the bend information calculation unit 110. In addition, the light detector driving unit 150 may be configured to also control the operation of the light source 310. The light detector driving unit 150 transmits the generated drive signal to the output unit 160.

The output unit 160 outputs, to the display unit 180, the bend information of the detection target portion group 410, which is acquired from the bend information calculation unit 110, or the bend information of the insertion portion 812, which is acquired from the endoscope bend information computing unit 140. In addition, the output unit 160 outputs the acquired bend information to the endoscope control unit 820. In addition, the output unit 160 outputs, to the light detector 320, the drive signal from the light detector driving unit 150.

Operations of the endoscope system 1 and the estimation device 10 are described according to an example embodiment of the present invention.

A user inserts the insertion portion 812 of the endoscope 810 into the insertion target body. At this time, the insertion portion 812 bends to form a shape of the insertion target body. The endoscope 810 obtains an image signal from the observation optical system and the imaging device provided in the insertion portion 812. The obtained image signal is transmitted to the image processing unit 822 of the endoscope control unit 820. The image processing unit 822 generates an image of the inside of the insertion target body, based on the acquired image signal. The image processing unit 822 displays the generated image on the display unit 180.

When the user causes the bend information of the insertion portion 812 to be displayed on the display unit 180 or wants to cause the endoscope control unit 820 to perform various operations using the bend information of the insertion portion 812, the user inputs such instructions into the control unit 100 via the input device 190. At this time, the estimation device 10 operates.

When the estimation device 10 operates, the light source 310 of the sensor driving unit 300 emits light in a predetermined emission wavelength range. The light emitted from the light source 310 is guided to the light guiding member 420 of the sensor unit 400 via the light branching unit 330. The guided light is transmitted into the light guiding member 420 from the base end side to the front end side. At this time, a light quantity in the light guiding member 420 is changed, depending on the bending state of the detection target portion group 410 provided in the light guiding member 420 and, thus, a light quantity to be transmitted is changed for each wavelength. The light is reflected and returns from the reflective member 430 and is transmitted into the light guiding member 420 from the front end side to the base end side. The reflected light reaches the light detector 320 via the light branching unit 330. The light detector 320 detects the intensity of the reflected light for each wavelength.

The light detector 320 outputs, to the input unit 130 of the control unit 100, the light quantity information about the wavelength and the intensity of the detected light. The bend information calculation unit 110 acquires the input light quantity information from the input unit 130, and the bend information calculation unit 110 calculates the bend information of the detection target portion group 410.

The endoscope bend information computing unit 140 acquires the calculated bend information of the detection target portion group 410. The endoscope bend information computing unit 140 calculates the bend information of the insertion portion 812 based on the acquired bend information.

The endoscope control unit 820 acquires, via the output unit 160, the bend information of the detection target portion group 410, which is calculated in the bend information calculation unit 110, or the bend information of the insertion portion 812, which is calculated in the endoscope bend information computing unit 140. The endoscope control unit 820 controls an operation of the endoscope 810 based on the acquired bend information. In addition, the bend information is displayed on the display unit 180 via the output unit 160.

Further, the light detector driving unit 150 acquires the information input to the input unit 130 and the bend information of the detection target portion group 410 which is calculated in the bend information calculation unit 110. The light detector driving unit 150 transmits the drive signal to the light detector 320 via the output unit 160 based on the acquired information and controls the operation of the light detector 320.

As described above, according to the estimation device 10, the bend information of the detection target portion group 410 is acquired by the calculation unit 101. Further, the endoscope bend information computing unit 140 calculates the bend information of the insertion portion 812 based on the acquired bend information. In this manner, it is possible for the user to know the bend information of the detection target portion group 410 or the insertion portion 812 during the manipulation of the endoscope 810. In addition, the endoscope control unit 820 is capable of controlling the operation of the endoscope 810 based on the bend information.

The calculation performed in the calculation unit 101 in the estimation device 10 of the embodiment is described in detail.

First, information prepared before use of the estimation device 10 is described. A detected light quantity (detected light quantity information) $D_{\lambda,n}$ with respect to light having a wavelength $\lambda n$, which is detected by the light detector 320, is given by the following Expression (1).

$$D_{\lambda,n} = E_{\lambda,n} \times A_{\lambda,n} \times B_{\lambda,n} \times C_{\lambda,n} \qquad \text{Expression (1)}$$

Here, $E_{\lambda,n}$ is an emitted light quantity with respect to the light having the wavelength $\lambda n$ which is emitted from the light source 310, $A_{\lambda,n}$, is an absorption rate of the light having the wavelength $\lambda n$ in the first light absorber 424, $B_{\lambda,n}$ is an absorption rate of the light having the wavelength $\lambda n$ in the second light absorber 425, $C_{\lambda,n}$ is an absorption rate of the light having the wavelength $\lambda n$ in a member other than the detection target portion group 410, which is positioned on a light path through which the light is transmitted, such as the light branching unit 330, the light guiding member 420, the reflective member 430, or the like in the sensor driving unit 300 and in the sensor unit 400.

The emitted light quantity $E_{\lambda,n}$ and the absorption rate $C_{\lambda,n}$ do not depend on a bending orientation or a magnitude of the bending of the detection target portion group 410. Hence, Expression (1) representing the detected light quantity $D_{\lambda,n}$ is rewritten as Expression (2), below. In other words, in a case where the detection target portion group 410 (detection target portions 411 and 412) has a predetermined shape as a reference (hereinafter, referred to as a reference bending state), a light quantity with respect to the light having the wavelength $\lambda n$, which is detected by the light detector 320, is obtained as a reference light quantity (or a reference light intensity value) $I_{\lambda,n}$. In addition, when the detection target portion group 410 bends with respect to the reference bending state, a ratio of the reference light quantity $I_{\lambda,n}$ and the light quantity with respect to the light having the wavelength $\lambda n$, which is detected by the light detector 320, is a change rate $\alpha_{\lambda,n}$ in the detection target portion group 410. In other words, the change rate $\alpha_{\lambda,n}$ is a change rate of the light quantity at which the first detection target portion 411 and the second detection target portion 412 that configure the detection target portion group 410 absorb the light. Accordingly, the light quantity $D_{\lambda,n}$ is given by the following Expression (2).

$$D_{\lambda,n} = I_{\lambda,n} \times \alpha_{\lambda,n} \qquad \text{Expression (2)}$$

The absorption rate of the light in the light absorbers 424 and 425 of the detection target portion group 410 changes depending on the bending orientation (e.g., the angle $\theta$ described above) and the magnitude of the bending (e.g., the curvature $\theta$) of the detection target portion group 410. Hence, the change rate $\alpha_{\lambda,n}$ in the detection target portion group 410 is given in the following Expression (3).

$$\alpha_{\lambda,n} \approx f_{\lambda,n}(\theta, \kappa) \qquad \text{Expression (3)}$$

Here, the function $f_{\lambda_n}$ is the bend characteristic information with respect to the detection target portion group 410.

The following Expression (4) is obtained by Expression (2) and Expression (3). In Expression (4), the left side represents the light quantity information in an arbitrary bending state, and the right side represents the light quantity estimation value obtained based on the reference light quantity (reference light quantity information) and the bend characteristic information.

$$D_{\lambda_n}(\theta,\kappa) \approx I_{\lambda_n} \times f_{\lambda_n}(\theta,\kappa) \qquad \text{Expression (4)}$$

In the reference bending state for determining the reference light quantity $I_{\lambda_n}$, for example, in a case where the detection target portion group 410 has the straight line shape (i.e., the curvature of the detection target portions 411 and 412 is 0), a case where the curvature radius is ∞ is employed. However, the reference bending state is not limited thereto and may have a shape other than the straight lint shape. Hereinafter, a case where the detection target portion group 410 has the straight line shape as the reference bending state is described. Note that the angle θ described above of the detection target portion group 410 having the straight line shape is 0 for convenience.

FIG. 10 is a diagram illustrating an example of a relationship between the wavelength and the reference light quantity. When the detection target portion group 410 is in the reference bending state (i.e., θ=0, κ=0), the light quantity $D_{\lambda_n}(0, 0)$ is given by the following Expression (5), by definition.

$$D_{\lambda_n}(0,0) = I_{\lambda_n} \qquad \text{Expression (5)}$$

In other words, the reference light quantity is $I_{\lambda_n}$ and $f_{\lambda_n}(0, 0)=1$, by definition.

In addition, the function $f_{\lambda_n}(\theta, \kappa)$ is given by the following Expression (6) derived from Expression (4).

$$f_{\lambda_n}(\theta, \kappa) \approx \frac{D_{\lambda_n}(\theta, \kappa)}{I_{\lambda_n}} \qquad \text{Expression (6)}$$

The function $f_{\lambda_n}$ as the bend characteristic information is acquired by changing the angle θ and the curvature κ in a range in which it is possible to obtain the angle θ and the curvature κ described above of the detection target portion group 410.

FIG. 11 is a diagram illustrating an example of bend characteristic information $f_{\lambda_1}(\theta, \kappa_1)$ and bend characteristic information $f_{\lambda_1}(\theta, \kappa_2)$ acquired with respect to the first wavelength λ1. FIG. 12 is a diagram illustrating an example of bend characteristic information $f_{\lambda_2}(\theta, \kappa_1)$ and bend characteristic information $f_{\lambda_2}(\theta, \kappa_2)$ acquired with respect to the second wavelength λ2. As described above, an amplitude and a phase vary by the wavelength and, thereby, it is possible to derive the angle θ and the curvature κ. FIGS. 11 and 12 illustrate bend characteristic information with respect to two curvatures $\kappa_1$ and $\kappa_2$, respectively. However, the acquired bend characteristic information is not limited thereto and may be acquired as relationships between the angle θ in the emission wavelength range and the change rate $\alpha_{\lambda_n}$ in the detection target portion group 410 with respect to various curvatures κ.

The function $f_{\lambda_n}$ as the bend characteristic information can be represented by a periodic function and, for example, can be approximately represented by a sine function of the following Expression (7).

$$f_{\lambda_n}(\theta,\kappa) = \alpha_{\lambda_n}(\kappa) \cdot \sin[\theta + b_{\lambda_n}(\kappa)] + c_{\lambda_n}(\kappa) \qquad \text{Expression (7)}$$

Here, $\alpha_{\lambda_n}$ represents amplitude, $b_{\lambda_n}$ represents a phase, and $c_{\lambda_n}$ is an offset. Since the terms are all the functions of the curvature κ, for example, it is possible to express Expression (7) in a quadratic equation of the curvature κ as the following Expression (8).

$$f_{\lambda_n}(\theta,\kappa) = (a_{2\lambda_n}\kappa^2 + a_{1\lambda_n}\kappa + a_{0\lambda_n})\sin[\theta + (b_{2\lambda_n}\kappa^2 b_{1\lambda_n}\kappa + b_{0\lambda_n})] + (c_{2\lambda_n}\kappa^2 + c_{1\lambda_n}\kappa + c_{0\lambda_n}) \qquad \text{Expression (8)}$$

Note that the periodic function is not limited to an expression represented by a first-order sine wave and, for example, in a case of using a Fourier series obtained by combining high-order sine waves as the function $f_{\lambda_n}$ accuracy thereof improves.

In example embodiments of the present invention, the bend characteristic information and the reference light quantity information are acquired in advance, for example, at the time of manufacturing the endoscope system 1 or at the time of assembly of the endoscope system 1, and are stored in the storage unit 120 in advance. Otherwise, in other example embodiments of the present invention, the bend characteristic information and the reference light quantity information may be acquired whenever the information is used.

Next, the calculation performed in the calculation unit 101 during the operation of the estimation device 10 will be described in detail. As illustrated in FIG. 13, the flexible portion 819 having the length L, which includes the detection target portion group 410, bends at an angle θ and with curvature κ. FIG. 14 is a diagram illustrating an example of the relationship between the wavelength and the detected light quantity in the bending state.

By Expression (4), the detected light quantity $D_{\lambda_n}$ detected by the light detector 320 is equal to the product of the reference light quantity information $I_\lambda$ acquired in advance (which is illustrated in FIG. 10) and the bend characteristic information $f_\lambda(\theta, \kappa)$ in the detection target portion group 410 (i.e., the change rate).

FIG. 15 is a diagram illustrating an example of such a change rate (i.e., the change rate $f_\lambda(\theta, \kappa)$) with respect to the reference light quantity information in an arbitrary bending state. As illustrated in FIG. 15, in order to obtain the angle θ and the curvature κ in the detection target portion group 410, a simultaneous equation represented by the following Expression (9) is solved, based on the detected light quantities $D_{\lambda_1}$ and $D_{\lambda_2}$ with the first wavelength λ1 and the second wavelength λ2 which are detected by the light detector 320.

$$\begin{cases} D_{\lambda_1}(\theta, \kappa) = I_{\lambda_1} \times f_{\lambda_1}(\theta,\kappa) \\ D_{\lambda_2}(\theta, \kappa) = I_{\lambda_2} \times f_{\lambda_2}(\theta,\kappa) \end{cases} \qquad \text{Expression (9)}$$

The reference light quantity information $I_{\lambda_1}$ and $I_{\lambda_2}$ and the bend characteristic information $f_{\lambda_1}(\theta, \kappa)$ and $f_{\lambda_2}(\theta, \kappa)$ are acquired in advance as described above and are stored in the storage unit 120. Hence, it is possible to obtain the angle θ and the curvature κ of the detection target portion group 410 (i.e., the bending orientation and the magnitude of the bending thereof) based on the detected light quantities $D_{\lambda_1}$ and $D_{\lambda_2}$. In other words, the light quantity estimation value is calculated based on a light quantity estimation relationship represented in a form of the function described above and, thereby, the bend information of the detection target portion group 410 is obtained. Note that the light quantity estimation relationship is not limited to the relationship represented by the form of the function described above and may be a relationship represented by a table (e.g., a lookup table) in which the relationship between the wavelength and the light quantity is stored.

In addition, bend information estimating calculation using, as the curvature, a parameter representing the magnitude of the bending of the detection target portion group and the bend characteristic is described. However, it is possible to employ bend information estimating calculation using another parameter such as the curvature radius as the parameter representing the magnitude of the bending and the bend characteristic information corresponding thereto.

FIG. 16 is a flowchart illustrating a process in the control unit 100 according to an example embodiment of the present invention. In Step S1, the control unit 100 determines whether or not the bend characteristic information is stored in the storage unit 120. In a case of determining that the information is not stored (NO), the process proceeds to Step S2 and the control unit 100 acquires the bend characteristic information (described below with reference to FIG. 17).

After the acquisition of the bend characteristic information in Step S2, or in a case where it is determined that the bend characteristic information is stored in the storage unit 120 in Step S1 (YES), the process proceeds to Step S3. Note that a case where the determination is YES in Step S1 means, for example, a case where the acquisition of the bend characteristic information is performed in the factory setting or at the time of assembly of the endoscope system 1.

In Step S3, the control unit 100 determines whether or not there is a request for reacquiring the reference light quantity information. In a case of determining that there is a request (YES), the process proceeds to Step S4. In Step S4, the control unit 100 acquires the reference light quantity information through a subroutine (Step S21 below with reference to FIG. 17 and Steps S211 to S213 described below with reference to FIG. 18) for acquiring the reference light quantity information described above. Note that there is a request for such reacquisition, for example, in a case where connection to another control unit other than the control unit 100 described above is performed, or in a case where the sensor driving unit 300 and the sensor unit 400 are separated from each other and are reconnected to each other.

The request for reacquisition of the reference light quantity information which is determined in Step S3 is issued, for example, in a case where the light branching unit 330 of the sensor driving unit 300 and the light guiding member 420 of the sensor unit 400 are separated from each other or are reconnected to each other. The control unit 100 may be configured to determine whether the connection is maintained, that is, the separation and the reconnection are performed in this case.

After the reference light quantity information $I_\lambda$ is acquired in Step S4, or in a case of determining that there is no request in Step S3 (NO), the process proceeds to Step S5 and the calculation unit 101 of the control unit 100 performs the bend information calculation of the detection target portion group 410.

After the bend information calculation process in Step S5 the process proceeds to Step S6. In Step S6, the control unit 100 determines whether or not calculation of the bend information is performed. In a case of determining that the calculation is performed (YES), the process returns to Step S1, and the processes from Step S1 described above are repeated. In a case of determining that the calculation is not performed (NO) the process ends.

FIG. 17 is a flowchart illustrating an example of acquisition of the bend characteristic information. In Step S21, the control unit 100 acquires the reference light quantity information $I_\lambda$. In Step S22, the control unit 100 acquires the bend characteristic information $f_{\lambda,n}(\theta, \kappa)$ of the detection target portion group 410. For example, the acquired bend characteristic information is the bend characteristic information $f_{\lambda,1}(\theta, \kappa_1)$ and $f_{\lambda,1}(\theta, \kappa_2)$ illustrated in FIG. 11, and is the bend characteristic information $f_{\lambda,2}(\theta, \kappa_1)$ and $f_{\lambda,2}(\theta, \kappa_2)$ illustrated in FIG. 12. For example, it is possible to acquire the items of the bend characteristic information by manually changing the bending orientation with the curvatures $\kappa_1$ and $\kappa_2$ with respect to the characteristic wavelengths $\lambda 1$ and $\lambda 2$, or mechanically changing by a bend setting mechanism not illustrated. Further, In Step S23, the acquired bend characteristic information is stored in the storage unit 120. The acquisition of bend characteristic information ends.

FIG. 18 is a flowchart illustrating an example of acquisition of the reference light quantity information. In Step S211, the control unit 100 sets that the detection target portion group 410 is in the reference bending state (a straight line shape in the embodiment). Note that, in a case where setting of the detection target portion group 410 in the reference bending state is manually performed, in Step S211, the control unit 100 checks whether or not the detection target portion group 410 is in the reference bending state. In Step S212, the control unit 100 acquires the light quantity information $I_\lambda$ in the reference bending state (Expression (5)). In Step S213, the acquired reference light quantity information $I_\lambda$ is stored in the storage unit 120. The acquisition of the reference light quantity information $I_\lambda$ is ended, and the process proceeds to Step S22.

FIG. 19 is a flowchart illustrating an example of a bend information calculation process. In Step S51, the bend information calculation unit 110 reads, from the storage unit 120, the reference light quantity information $I_\lambda$ and the bend characteristic information $f_{\lambda,n}(\theta, \kappa)$ of the detection target portion group 410. In Step S52, the bend information calculation unit 110 acquires, via the input unit 130, the detected light quantity information $D_{\lambda,n}$ in an arbitrary bending state by the light detector 320. Further, in Step S53, the bend information calculation unit 110 obtains the angle $\theta$ and the curvature $\kappa$ in an above-mentioned manner, based on the detected light quantity information $D_{\lambda,n}$, the reference light quantity information $I_\lambda$, and the bend characteristic information $f_{\lambda,n}(\theta, \kappa)$ (Expression (9)). In Step S54, the bend information calculation unit 110 transmits the obtained angle $\theta$ and the curvature $\kappa$ to the output unit 160. The bend information calculation is ended.

Note that the bend characteristic information does not depend on the characteristics of the light source 310 or the light detector 320 but depends on only the light absorption characteristics of the light absorbers 424 and 425 of the detection target portion group 410. Hence, components of the sensor driving unit 300 may be separated from one another and, for example, a light source that emits light in a predetermined emission wavelength range or a light detector having detection sensitivity over all of the wavelengths which are required by the control unit 100 may be used. In other words, it is possible to acquire the bend characteristic information by another light source or light detector or it is possible to perform replacement with another sensor driving unit.

According to example embodiments of the present invention, the light guiding member 420 that configures the sensor unit 400 is provided with the detection target portion group 410 including the plurality of detection target portions formed substantially at the same position in the longitudinal direction of the light guiding member. Thus, in order to estimate the bend information of the detection target portion group 410, the wavelengths are used and the number of wavelengths is greater than or equal to the number of detection target portions. The light quantity information for each wavelength in the detection target portion group 410 is detected by the light detector 320 of the sensor driving unit 300. The bend information of the detection target portion group 410 or the insertion portion 812 is estimated based on the detected light quantity information and the light quantity estimation value calculated based on the light quantity estimation relationship including the bend characteristic information stored in advance in the storage unit 120. As described above, according to the embodiment, it is possible to provide the bend information estimation device that is capable of estimating the bend information.

In addition, according to example embodiments of the present invention, it is possible to obtain the bend information of the detection target portion group 410 without obtaining the bend information of the individual detection target portions that configure the detection target portion group 410.

In addition, according to example embodiments of the present invention, in order to obtain the bend information, the change rate of the light in the detection target portion group 410 is used. Hence, it is possible to perform the bend information calculation without depending on a spectrum of the light source 310 of the sensor driving unit 300 or spectral sensitivity of the light detector 320.

In addition, according to example embodiments of the present invention, information about a distance between the light source 310 and the detection target portion group 410 provided in the light guiding member 420 is not required in the bend information calculation. Hence, it is possible to perform the bend information calculation without considering a positional relationship between the light source 310 and the detection target portion group 410.

Further, according to example embodiments of the present invention, absorption or loss of the light in the light branching unit 330 of the sensor driving unit 300 and the reflective member 430 of the sensor unit 400 is constant regardless of the magnitude of the bending of the detection target portion group 410. Hence, even the reference light quantity information is obtained in a state in which the loss is reflected in the calculation. Therefore, it is possible to perform computation without considering specifically the effects of the light branching unit 330 or the reflective member 430.

FIG. 20 is a block diagram illustrating an example configuration of the sensor 500. As illustrated in FIG. 20, the sensor unit 400 includes a sensor storage unit 440. The sensor storage unit 440 stores sensor identification information or the bend characteristic information in advance in factory setting or at the time of assembly of the device. The sensor identification information (i.e., ID information) is information for identifying types of or individual sensor units 400, and the information is preferably unique. In addition, in acquisition of the bend characteristic information, the bend characteristic information is stored in the sensor storage unit 440 (e.g., Step S213 in FIG. 18). In this manner, even in a case where the sensor unit 400 is connected to another sensor driving unit other than the sensor driving unit 300, it is possible to read the sensor identification information or the bend characteristic information from the sensor storage unit 440.

In addition, in the case of the connection to another control unit (in a case where the bend characteristic information is not present in the storage unit 120), the bend characteristic information is read from the sensor storage unit 440 instead of performing the acquisition of the bend characteristic information (e.g., Step S22 in FIG. 17). In this manner, even in the case where the sensor driving unit 300 is connected to another control unit the bend characteristic information does not need to be reacquired.

According to an example embodiment using a plurality of sensor units, before Step S1 and immediately after the start of the flow illustrated in FIG. 16, the control unit 100 may set a step of checking the sensor identification information of the connected sensor units 400. Note that, in this example embodiment, as prerequisites, the bend characteristic information is associated with the sensor identification information and the bend characteristic information (i.e., bend characteristic information for each of the plurality of sensor units) is stored in the storage unit 120.

In the step of checking the sensor identification information, for example, the sensor identification information is input by the input device 190 from the input unit 130. The sensor identification information may be engraved or attached on the sensor unit 400 or may be stored in a tag. The tag is preferably a non-contact tag such as RFID. Otherwise, the information may be stored in and read from the sensor storage unit 440 as described above or the information stored in another storage medium may be read. In addition, in a case of the sensor identification information that does not satisfy the prerequisites described above and is not stored in the storage unit 120, the process may be performed along the flow in FIG. 16.

According to an example embodiment of the present invention, because it is possible to extract the bend characteristic information from the sensor identification information it also is possible to extract the bend characteristic information from the sensor identification information even in the case of connection to another sensor unit. Hence, the bend characteristic information does not need to be reacquired.

Expression (9) may be expressed by log and may be expressed as the following Expression (10).

$$\begin{cases} \log D_{\lambda 1}(\theta, \kappa) = \log I_{\lambda 1} + \log f_{\lambda 1}(\theta, \kappa) \\ \log D_{\lambda 2}(\theta, \kappa) = \log I_{\lambda 2} + \log f_{\lambda 2}(\theta, \kappa) \end{cases} \quad \text{Expression (10)}$$

Log is used and the right side of Expression (9) is expressed by addition. Therefore, it is possible to consider log of the change rate of the detection target portion group 410 as absorbance obtained from the reference light quantity information as a reference. In addition, the bend characteristic information of the detection target portion group 410 is represented by the following Expression (11) using log of Expression (3).

$$F_{\lambda,n}(\theta,\kappa) \approx \log f_{\lambda,n}(\theta,\kappa) \quad \text{Expression (11)}$$

The following Expression (12) is obtained from Expression (10) and Expression (11).

$$\begin{cases} \log D_{\lambda 1}(\theta, \kappa) = \log I_{\lambda 1} + \log F_{\lambda 1}(\theta, \kappa) \\ \log D_{\lambda 2}(\theta, \kappa) = \log I_{\lambda 2} + \log F_{\lambda 2}(\theta, \kappa) \end{cases} \quad \text{Expression (12)}$$

According to an example embodiment of the present invention, because it is possible to rewrite a product of the reference light quantity information and the bend characteristic information into a sum thereof, it is possible to easily perform computation.

FIG. 21 is a diagram illustrating an example of a relationship between the wavelength and the absorption rate of light in the first light absorber and the second light absorber. It should be understood that the wavelengths used to calculate the bend information are not limited to the specific wavelengths λ1 and λ2 and may be a first wavelength band $d_{\lambda,1}$ and a second wavelength band $d_{\lambda,2}$ having bandwidths, respectively, as illustrated in FIG. 21. For example, the first detection target portion 411 and the second detection target portion 412 may have the wavelength bands (i.e., characteristic absorption bands) as wavelength ranges having absorption wavelength characteristics different from each other (i.e., the absorption rates of the first light absorber and the second light absorber are different from each other) in a wavelength range in which both of the portions absorb light (i.e., both of the first light absorber and the second light absorber have the absorption rate in the wavelength range). In example embodiments of the present invention, the number of the wavelength bands is greater than or equal to the number of the detection target portions (i.e., two or more).

According to an example embodiment of the present invention, because the wavelength that is used to calculate the bend information is not one specific wavelength but may have a bandwidth, the light detector 320 does not need to have high wavelength resolution. Hence, it is possible to manufacture the light detector 320 at low costs. In addition, because only a local wavelength is not used, the light detector is unlikely to be affected by noise. In addition, the wavelength band which is used may include a part of another wavelength band. For example, the first wavelength band and the second wavelength band may overlap each other.

FIG. 22 is a block diagram illustrating an example of a configuration of the sensor driving unit 300 and the sensor unit 400. The sensor driving unit 300 includes the light source 310 and the light detector 320. In addition, the sensor unit 400 includes the light guiding member 420 which is provided with the detection target portion group 410. The light branching unit 330, the antireflective member 340, and the reflective member 430 described above are not provided. The light source 310 is optically connected to the base end of the light guiding member 420. In addition, the light detector 320 is optically connected to the front end of the light guiding member 420. The light emitted from the light source 310 is guided to the light guiding member 420. The guided light is transmitted into the light guiding member 420 from the base end side to the front end side, and then reaches the light detector 320. In this example embodiment in which the light branching unit, the antireflective member, and the reflective member are not provided, it is possible to reduce the loss of the light due to these members. Therefore, it is possible to reduce the light quantity of the light source.

In certain example embodiments of the present invention, the light detector 320 may be configured to be capable of detecting a plurality of predetermined wavelengths λ1 and λ2, or the light quantities $D_{\lambda,1}$ and $D_{\lambda,2}$ of the wavelength bands $d_{\lambda,1}$ and $d_{\lambda,2}$, respectively. For example, wavelength characteristics of emission intensity of the light guided to the light guiding member 420 is caused to change at a time, and a light quantity at the time is detected.

FIG. 23 is a diagram illustrating an example of the relationship between the wavelength and the emission intensity of the light source at times t1 and t2. In FIG. 23, a relationship at the time t1 is illustrated in a solid line and a relationship at the time t2 is illustrated in a dashed line. The light source 310 emits light having a peak in the wavelength λ1 at time t1 and light having a peak in the wavelength λ2 at time t2, using a filter and the like.

FIG. 24 corresponds to FIG. 23 and is a diagram illustrating a relationship between the wavelength of light incident to the light detector and the detection sensitivity of the light detector. The light detector 320 includes a light receiving element (light receiving element that does not have a light dispersing function performed by a filter or the like) that has detection sensitivity with respect to the intensity of the light having peaks in the wavelengths λ1 and λ2. According to this example embodiment of the present invention, the light quantities are detected from the light receiving element synchronized at the times t1 and t2 and, thereby, it is possible to obtain the light quantity information (detected light quantities of the wavelength bands).

A further embodiment of the present invention is described with reference to FIGS. 25 and 26 and, hereinafter, description of parts common to the previously described embodiments is omitted and only different parts are described.

FIG. 25 is a block diagram illustrating an example of a bend information calculation unit 110a according to an example embodiment of the present invention. The bend information calculation unit 110a includes the estimation value calculation unit 212 and an evaluation value calculation unit 214 as an optimized calculation portion. As will be described below, the evaluation value calculation unit 214 performs calculation to optimize the bend information of the detection target portion group 410.

As illustrated in the example embodiment of FIG. 25, the bend information of the detection target portion group 410 is estimated by using the relationship between the wavelength and the absorption rate of the light in the first light absorber and the second light absorber similar to the embodiments described above, and further using detected light quantity information $D_{\lambda,3}$ in a third wavelength λ3, the reference light quantity information $I_{\lambda,3}$, and bend characteristic information $f_{\lambda,3}$ of the detection target portion group 410.

FIG. 26 is a diagram illustrating an example of a relationship between the wavelength and the absorption rate of the light in the first light absorber and the second light absorber according to an example embodiment of the present invention. The third wavelength λ3 is a wavelength having absorption rate of the light which is different from the first wavelength λ1 and the second wavelength λ2.

According to the example embodiment of FIGS. 25 and 26, a difference $\Delta_{\lambda,n}$ between the right side and the left side in Expression (9) is obtained (n=1, 2, and 3). In other words, the following Expression (13) represents a difference between a value of the light quantity information and an estimated light quantity value in an arbitrary bending state.

$$\Delta_{\lambda_n} = D_{\lambda_n}(\theta,\kappa) - I_{\lambda_n} \times f_{\lambda_n}(\theta,\kappa) \quad \text{Expression (13)}$$

In the example embodiment of FIGS. 25 and 26, in Step S53 in the flow illustrated in FIG. 19, the evaluation value calculation unit 214 optimizes the bend information of the detection target portion group 410 such that the difference between the value of the light quantity information and the estimated bend information is small. For example, an evaluation value J as a sum of squared differences $\Delta_{\lambda,n}$ in the wavelengths is obtained, and the bend information of the detection target portion group 410 is determined to have the minimum evaluation value J. The evaluation value J is given by the following Expression (14).

$$J = \sum (\Delta_{\lambda_n})^2 \quad \text{Expression (14)}$$
$$= \Delta_{\lambda_1}^2 + \Delta_{\lambda_2}^2 + \Delta_{\lambda_3}^2$$

In addition, for example, as will be shown in the following Expression (15), in certain example embodiments, a weighting coefficient $w_n$ may be applied and contribution of the evaluation value J for each wavelength or wavelength band may be adjusted.

$$J = \sum w_n (\Delta_{\lambda_n})^2 \quad \text{Expression (15)}$$
$$= w_1 \Delta_{\lambda_1}^2 + w_2 \Delta_{\lambda_2}^2 + w_3 \Delta_{\lambda_3}^2$$

In setting of the weighting coefficient $w_n$, for example, contribution of the wavelength or the wavelength band in which the maximum light absorption amount is obtained by the light absorbers of the detection target portion group 410 may be increased.

According to the certain example embodiments, the evaluation value calculation unit 214 performs the optimized calculation, and thereby the bend information of the detection target portion group 410 is obtained with high accuracy. In addition, it is possible to provide the bend information estimation device that has redundancy and is unlikely to be affected by noise or the like.

In addition, in some example embodiments, the optimized calculation can include a plurality of optimized calculations which are different in convergence. For example, a first optimized calculation is an overall optimized calculation with high accuracy and a second optimized calculation is a locally optimized calculation with higher convergence than the first optimized calculation. The overall optimized calculation means a method such as particle swarm optimization (PSO), differential evolution (DE), a genetic algorithm (GA), and a simulated annealing method (SA), which can derive an optimal solution without obtaining a local solution. The locally optimized calculation means a local search method such as Newton's method, a method of steepest descent, or a simplex method, which obtains a local solution. It is possible to configure the bend information estimation device such that a user can select whether to perform any calculation or to perform parallel calculations. As described above, the user can select accuracy and a speed of the calculation. For example, use of the parallel calculations enables to calculate the appropriate optimal solution rapidly.

A further example embodiment of the present invention is described with reference to FIGS. 27 to 31. Hereinafter, description of parts common to the previous embodiments is omitted, and only different parts are described.

FIG. 27 is a block diagram illustrating an example of a configuration of the sensor 500 configured to have the sensor driving unit 300 and the sensor unit 400. The light guiding member 420 is provided with a first detection target portion group 410 including the first detection target portion 411 and the second detection target portion 412 and a second detection target portion group 450 including a third detection target portion 451 and a fourth detection target portion 452. The second detection target portion group 450 is disposed at a different position from the first detection target portion group 410 in the longitudinal direction of the light guiding member 420. The second detection target portion group 450 is formed in a similar way to the first detection target portion group 410. The third detection target portion 451 is provided with a third light absorber and the fourth detection target portion 452 is provided with a fourth light absorber. A positional relationship between the third detection target portion 451 and the fourth detection target portion 452 is similar to the positional relationship between the first detection target portion 411 and the second detection target portion 412.

FIG. 28 is a diagram illustrating another example of the relationship between the wavelength and the absorption rate of light in first to fourth light absorbers. As illustrated in FIG. 28, the light absorbers provided in different detection target portions 411, 412, 451, and 452 have a light absorption rate different for each wavelength, that is, have light absorption characteristics different from each other.

Next, calculations performed in the calculation unit 101 of the estimation device 10 in order to estimate the bend information (angle $\theta_\alpha$ and curvature $\kappa_\alpha$) in the first detection target portion group 410 and the bend information (angle $\theta_\beta$ and curvature $\kappa_\beta$) in the second detection target portion group 450 are described. A length $L_1$ of the flexible portion 819 including the first detection target portion group 410 and a length $L_2$ thereof including the second detection target portion group 450 are considered to bend at angles $\theta_1$ and $\theta_2$ and with curvatures $\kappa_1$ and $\kappa_2$, respectively, as illustrated in FIGS. 29A and 29B.

Note that, as illustrated in FIGS. 29A and 29B, the angles $\theta_1$ and $\theta_2$ are represented by a local coordinate system (i.e., an $x_1 y_1 z_1$ coordinate system and an $x_2 y_2 z_2$ coordinate system) in the detection target portion groups 410 and 450, respectively. Hence, the bending orientation is represented by, for example, the angle $\theta_1$ formed between an $x_1$ axis and a straight line through the origin $P_{10}$ (0, 0, 0) and a point (x, y, 0) obtained by projecting a point $P_{11}$ (x, y, z) to an xy plane as illustrated in FIG. 29A and the angle $\theta_2$ formed between an $x_2$ axis and a straight line through the origin $P_{20}$ (0, 0, 0) and a point (x, y, 0) obtained by projecting a point $P'_{21}$ (x, y, z) to the xy plane as illustrated in FIG. 29B. In addition, the magnitude of the bending is represented by, for example, the curvature $\kappa_1$ and the curvature $\kappa_2$.

Similar to Expression (2), by using the product of the reference light quantity $I_{\lambda,n}$ and the change rates $\alpha_{\lambda,n}$ and $\beta_{\lambda,n}$ in the detection target portion groups 410 and 450, the detected light quantity $D_{\lambda,n}$ detected by the light detector 320 is expressed as follows.

$$D_{\lambda_n} = I_{\lambda_n} \times \alpha_{\lambda_n} \times \beta_{\lambda_n} \quad \text{Expression (16)}$$

The change rate $\alpha_{\lambda,n}$ is a ratio of the reference light quantity $I_{\lambda,n}$ and the light quantity with respect to the light having the wavelength λn which is detected by the light detector 320 when only the first detection target portion group 410 bends with respect to the reference bending state (i.e., a change rate of the light quantity which is produced due to the absorption of the light by the first detection target portion 411 and the second detection target portion 412 that comprise the first detection target portion group 410). In addition, the change rate $\beta_{\lambda,n}$ is a ratio of the reference light quantity $I_{\lambda,n}$ and the light quantity with respect to the light having the wavelength λn which is detected by the light detector 320 when only the second detection target portion group 450 bends with respect to the reference bending state (i.e., a change rate of the light quantity which is produced due to the absorption of the light by the third detection target portion 451 and the fourth detection target portion 452 that comprise the second detection target portion group 450).

Similar to the first embodiment, the change rates $\alpha_{\lambda,n}$ and $\beta_{\lambda,n}$ are given in the following Expression (17) and Expression (18).

$$\alpha_{\lambda_n} \approx f_{\lambda_n}(\theta_\alpha, \kappa_\alpha) \quad \text{Expression (17)}$$

$$\beta_{\lambda_n} \approx g_{\lambda_n}(\theta_\beta, \kappa_\beta) \quad \text{Expression (18)}$$

Here, the function $f_{\lambda,n}$ is the bend characteristic information in the first detection target portion group 410 and the function $g_{\lambda,n}$ is the bend characteristic information in the second detection target portion group 450.

The following Expression (19) is obtained from Expression (16), Expression (17), and Expression (18). In Expression (19), the left side represents the light quantity information in an arbitrary bending state and the right side represents a light quantity estimation value generated based on a product of the reference light quantity (reference light quantity information) and the bend characteristic information of the first and second detection target portion groups.

$$D_{\lambda,n}(\theta_\alpha, \kappa_\alpha, \theta_\beta, \kappa_\beta) \approx I_{\lambda,n} \times f_{\lambda,n}(\theta_\alpha, \kappa_\alpha) \times g_{\lambda,n}(\theta_\beta, \kappa_\beta) \quad \text{Expression (19)}$$

In the reference bending state for determining the reference light quantity $I_{\lambda,n}$, for example, a case where both of the detection target portion groups 410 and 450 have the straight line shape (i.e., a case where the curvatures of the detection target portion groups 410 and 450 are 0) the curvature radius is ∞. Note that the angles $\theta_\alpha$ and $\theta_\beta$ of the detection target portion groups 410 and 450 are 0, for convenience. When the detection target portion groups 410 and 450 are in the reference bending state, the light quantity $D_{\lambda,n}(0, 0, 0)$ is given by the following Expression (20), by definition.

$$D_{\lambda,n}(0,0,0,0) = I_{\lambda,n} \quad \text{Expression (20)}$$

In other words, the reference light quantity is $I_{\lambda,n}$, and $f_{\lambda,n}(0, 0) = g_{\lambda,n}(0, 0) = 1$, by definition.

In addition, the function $f_{\lambda,n}(\theta_\alpha, \kappa_\alpha)$ and the function $g_{\lambda,n}(\theta_\beta, \kappa_\beta)$ are given by the following Expression (21) and Expression (22) derived from Expression (19).

$$f_{\lambda,n}(\theta_\alpha, \kappa_\alpha) \approx \frac{D_{\lambda,n}(\theta_\alpha, \kappa_\alpha, 0, 0)}{I_{\lambda,n}} \quad \text{Expression (21)}$$

$$g_{\lambda,n}(\theta_\beta, \kappa_\beta) \approx \frac{D_{\lambda,n}(0, 0, \theta_\beta, \kappa_\beta)}{I_{\lambda,n}} \quad \text{Expression (22)}$$

The function $f_{\lambda,n}$ and the function $g_{\lambda,n}$ as the bend characteristic information are acquired by changing the angles $\theta_\alpha$ and $\theta_\beta$ and the curvatures $\kappa_\alpha$ and $\kappa_\beta$ of the detection target portion groups 410 and 450 in a possible range, respectively. For example, the functions $f_{\lambda,1}(\theta_\alpha, \kappa_1)$, $f_{\lambda,1}(\theta_\alpha, \kappa_2)$. $f_{\lambda,2}(\theta_\alpha, \kappa_1)$ and $f_{\lambda,2}(\theta_\alpha, \kappa_2)$ as the bend characteristic information of the first detection target portion group 410 are the same as in FIGS. 11 and 12.

FIG. 30 is a diagram illustrating an example of bend characteristic information $g_{\lambda,1}(\theta_\beta, \kappa_1)$ and bend characteristic information $g_{\lambda,1}(\theta_\beta, \kappa_2)$ acquired with respect to the first wavelength $\lambda 1$. FIG. 31 is a diagram illustrating an example of bend characteristic information $g_{\lambda,2}(\theta_\beta, \kappa_1)$ and bend characteristic information $g_{\lambda,2}(\theta_\beta, \kappa_2)$ acquired with respect to the second wavelength $\lambda 2$. FIGS. 30 and 31 will be described in conjunction.

As described above, an amplitude and a phase vary depending on the wavelength and, thereby, it is possible to derive the angle $\theta_\beta$ and the curvature $\kappa$. The wavelengths used in the calculation in example embodiments are wavelengths $\lambda 1$, $\lambda 2$, $\lambda 3$, and $\lambda 4$ which are absorbed by the detection target portions 411, 412, 451, and 452. Hence, for example, the bend characteristic information $f_{\lambda,1}(\theta_\alpha, \kappa_1)$, $f_{\lambda,1}(\theta_\alpha, \kappa_2)$, $f_{\lambda,2}(\theta_\alpha, \kappa_1)$, $f_{\lambda,2}(\theta_\alpha, \kappa_2)$, $f_{\lambda,3}(\theta_\alpha, \kappa_1)$, $f_{\lambda,3}(\theta_\alpha, \kappa_2)$, $f_{\lambda,4}(\theta_\alpha, \kappa_1)$, and the bend characteristic information $g_{\lambda,1}(\theta_\beta, \kappa_1)$, $g_{\lambda,1}(\theta_\beta, \kappa_2)$, $g_{\lambda,2}(\theta_\beta, \kappa_1)$, $g_{\lambda,2}(\theta_\beta, \kappa_2)$, $g_{\lambda,3}(\theta_\beta, \kappa_1)$, $g_{\lambda,3}(\kappa_\beta, \kappa_2)$, $g_{\lambda,4}(\theta_\beta, \kappa_1)$, and $g_{\lambda,4}(\theta_\beta, \kappa_2)$ are acquired. It is possible to acquire the items of the bend characteristic information by manually changing the bending orientation with the curvatures $\kappa_1$ and $\kappa_2$ with respect to the characteristic wavelengths $\lambda 1$, $\lambda 2$, $\lambda 3$, and $\lambda 4$ or mechanically changing by a bend setting mechanism not illustrated.

In example embodiments, in order to obtain the angles $\theta_\alpha$ and $\theta_\beta$ and the curvatures $\kappa_\alpha$ and $\kappa_\beta$ in the first detection target portion group 410 and the second detection target portion group 450, a simultaneous equation represented by the following Expression (23) is solved based on the detected light quantities $D_{\lambda 1}$ to $D_{\lambda 4}$ in the first to fourth wavelengths $\lambda 1$ to $\lambda 4$ which are detected by the light detector 320.

$$\begin{cases} D_{\lambda 1}(\theta_\alpha, \kappa_\alpha, \theta_\beta, \kappa_\beta) = I_{\lambda 1} \times f_{\lambda 1}(\theta_\alpha, \kappa_\alpha) \times g_{\lambda 1}(\theta_\beta, \kappa_\beta) \\ D_{\lambda 2}(\theta_\alpha, \kappa_\alpha, \theta_\beta, \kappa_\beta) = I_{\lambda 2} \times f_{\lambda 2}(\theta_\alpha, \kappa_\alpha) \times g_{\lambda 2}(\theta_\beta, \kappa_\beta) \\ D_{\lambda 3}(\theta_\alpha, \kappa_\alpha, \theta_\beta, \kappa_\beta) = I_{\lambda 3} \times f_{\lambda 3}(\theta_\alpha, \kappa_\alpha) \times g_{\lambda 3}(\theta_\beta, \kappa_\beta) \\ D_{\lambda 4}(\theta_\alpha, \kappa_\alpha, \theta_\beta, \kappa_\beta) = I_{\lambda 4} \times f_{\lambda 4}(\theta_\alpha, \kappa_\alpha) \times g_{\lambda 4}(\theta_\beta, \kappa_\beta) \end{cases} \quad \text{Expression (23)}$$

As described above, it is possible to obtain the angles $\theta_\alpha$ and $\theta_\beta$ and the curvatures $\kappa_\alpha$ and $\kappa_\beta$ in the detection target portion groups 410 and 450 (i.e., the bend information) based on the detected light quantities $D_{\lambda 1}$ to $D_{\lambda 4}$. Similarly, it is possible to obtain the bend information of three or more detection target portion groups.

Throughout this description, an endoscope is described as an example of a device to which the bend information estimation device is applied, and the endoscope system is described; however, one of ordinary skill in the art will appreciate that a target in which the bend information estimation device is incorporated is not limited to an endoscope and may be any target for which bend estimation is desired (e.g., a catheter, a surgical robot, or the like, whether or not it is inserted into an insertion target body).

As described above, example embodiments of the present invention are described with reference to the accompanying drawings. However, it should be noted that all of these drawings and descriptions are presented only as exemplary embodiments. The present invention is not limited to the embodiments described above, and alternative embodiments may be conceived that may have a structure and method disclosed as herein without departing from the principle of the disclosure as claimed in the present disclosure.

What is claimed is:

1. An endoscope system comprising:
   a first light absorber associated with a position on a light guide, the first light absorber having a first light absorption rate and enabled to absorb first amounts of a plurality of wavelengths of a light transmitted along the light guide;
   a second light absorber associated with the position on the light guide, the second light absorber having a second light absorption rate different from the first light absorption rate and enabled to absorb second amounts, different from the first amounts, of the same plurality of wavelengths of the light transmitted along the light guide;
   a light detector enabled to detect respective intensities of the plurality of wavelengths of the light not absorbed by the first light absorber and the second light absorber; and
   a processor enabled to calculate a bend state of the light guide as a function of the light transmitted along the light guide, characteristics of the plurality of wavelengths of the lights, and the detected intensities of the plurality of wavelengths of the light.

2. The endoscope system of claim 1
wherein the light guide is enabled to be inserted into an endoscope; and
wherein the bend state of the light guide is indicative of a bend state of the endoscope.

3. The endoscope system of claim 1
wherein the first light absorber and the second light absorber comprise a detection target group; and
wherein the detected intensities of the plurality of wavelengths of the light not absorbed by the first light absorber and the second light absorber is indicative of a bend state of the light guide at the detection target group.

4. The endoscope system of claim 3 wherein the bend state of the light guide at the detection target group comprises:
a bend orientation about the axis of the light guide at the detection target group; and
a bend magnitude of the light guide at the detection target group.

5. The endoscope system of claim 4 further comprising memory configured to store relationships defining change rates of the detected light intensities according to bend states of the light guide at the detection target group.

6. The system of claim 5, wherein the relationships are stored at a time prior to use.

7. The system of claim 5, wherein the memory is configured to store reference light intensity values for the plurality of wavelengths of the light.

8. The system of claim 7 wherein the processor is further enabled to calculate the bend orientation and the bend magnitude according to the detected intensities of first and second wavelengths of the plurality of wavelengths of the light, reference light intensity values for the first and second wavelengths of the light, and the stored relationships.

9. The system of claim 7 wherein the processor is further enabled to calculate the bend state in an optimized calculation performed such that a minimum evaluation value is obtained based on a difference between each respective detected intensity of the plurality of wavelengths and each respective relationship and a contribution of each wavelength to the relationships of the detection target portion group.

10. The system of claim 7 further comprising:
a second detection target group comprising:
a third light absorber disposed on the light guide and enabled to absorb third amounts of a second plurality of wavelengths of the light transmitted along the light guide; and
a fourth light absorber disposed at a substantially same position as the third light absorber along the axis of the light guide and enabled to absorb respective fourth amounts of the second plurality of wavelengths of the light transmitted along the light guide;
wherein the light detector is further enabled to detect respective intensities of the second plurality of wavelengths of the light not absorbed by the first light absorber, the second light absorber, the third light absorber, and the fourth light absorber; and
wherein the processor is further enabled to calculate a second bend state of the light guide for the second detection target group according to the detected intensities of the second plurality of wavelengths of the light.

\* \* \* \* \*